United States Patent
Rothstein et al.

(10) Patent No.: US 10,500,046 B2
(45) Date of Patent: *Dec. 10, 2019

(54) DELIVERY SYSTEM HAVING RETRACTABLE WIRES AS A COUPLING MECHANISM AND A DEPLOYMENT MECHANISM FOR A SELF-EXPANDING PROSTHESIS

(71) Applicant: Medtronic, Inc., Minneapolis, MN (US)

(72) Inventors: Paul Rothstein, Elk River, MN (US); James R. Keogh, Maplewood, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 692 days.

This patent is subject to a terminal disclaimer.

(21) Appl. No.: 14/968,135

(22) Filed: Dec. 14, 2015

(65) Prior Publication Data

US 2017/0165065 A1 Jun. 15, 2017

(51) Int. Cl.
*A61F 2/24* (2006.01)
*A61F 2/966* (2013.01)
*A61F 2/82* (2013.01)

(52) U.S. Cl.
CPC .......... *A61F 2/2439* (2013.01); *A61F 2/2409* (2013.01); *A61F 2/2412* (2013.01);
(Continued)

(58) Field of Classification Search
CPC ...... A61F 2/2427; A61F 2/243; A61F 2/2436; A61F 2/2439; A61F 2/95; A61F 2/954;
(Continued)

(56) References Cited

U.S. PATENT DOCUMENTS 5,957,949 A 9/1999 Leonhardt et al.
6,425,916 B1 7/2002 Garrison et al.
(Continued)

FOREIGN PATENT DOCUMENTS

WO WO2006/005082 1/2006
WO WO2007/097983 8/2007
WO WO2014/081796 5/2014

OTHER PUBLICATIONS

PCT/US2016/065957, The International Search Report and the Written Opinion of the International Searching Authority, dated May 2, 2017.
(Continued)

*Primary Examiner* — Melanie R Tyson
(74) *Attorney, Agent, or Firm* — Medler Ferro Woodhouse & Mills PLLC

(57) ABSTRACT

A delivery system for transcatheter implantation of a heart valve prosthesis. The delivery system includes an outer sheath component defining a lumen therethrough, an elongate tube having at least two flat wires longitudinally extending from a distal end thereof, and self-expanding first and second frames disposed in series within a distal portion of the outer sheath component and held in a compressed delivery configuration therein. The elongate tube and the at least two flat wires are slidably disposed within the lumen of the outer sheath component. In the compressed delivery configuration the at least two flat wires longitudinally extend along exterior portions of the first and second frames and are woven through adjacent ends of the first and second frames to releasably couple them to each other. Proximal retraction of the at least two flat wires from the first and second frames releases at least the first frame from the delivery system.

20 Claims, 23 Drawing Sheets

(52) U.S. Cl.
CPC .......... *A61F 2/2418* (2013.01); *A61F 2/2427* (2013.01); *A61F 2/2436* (2013.01); *A61F 2/2469* (2013.01); *A61F 2/966* (2013.01); *A61F 2002/826* (2013.01); *A61F 2002/9665* (2013.01); *A61F 2230/0006* (2013.01); *A61F 2230/0069* (2013.01); *A61F 2250/006* (2013.01)

(58) Field of Classification Search
CPC .... A61F 2/962; A61F 2/966; A61F 2002/826; A61F 2002/9665; A61F 2002/9505; A61F 2002/9522
USPC ........................................................ 623/2.11
See application file for complete search history.

(56) References Cited

U.S. PATENT DOCUMENTS

| | | | |
|---|---|---|---|
| 6,623,518 B2 * | 9/2003 | Thompson | A61F 2/91 606/108 |
| 7,419,501 B2 | 9/2008 | Shiu et al. | |
| 7,749,266 B2 | 7/2010 | Forster et al. | |
| 8,167,932 B2 | 5/2012 | Bourang et al. | |
| 8,721,713 B2 | 5/2014 | Tower et al. | |
| 2003/0199971 A1 | 10/2003 | Tower et al. | |
| 2004/0098081 A1 | 5/2004 | Landreville et al. | |
| 2005/0137687 A1 | 6/2005 | Salahieh et al. | |
| 2005/0288766 A1 * | 12/2005 | Plain | A61F 2/95 623/1.12 |
| 2008/0269877 A1 | 10/2008 | Jenson et al. | |
| 2010/0249915 A1 | 9/2010 | Zhang | |
| 2011/0257718 A1 | 10/2011 | Argentine | |
| 2011/0270371 A1 | 11/2011 | Argentine | |
| 2011/0270372 A1 | 11/2011 | Argentine | |
| 2014/0142691 A1 * | 5/2014 | Pouletty | A61F 2/24 623/2.11 |

OTHER PUBLICATIONS

PCT/US2016/065983, The International Search Report and the Written Opinion of the International Searching Authority, dated Apr. 5, 2017.

* cited by examiner

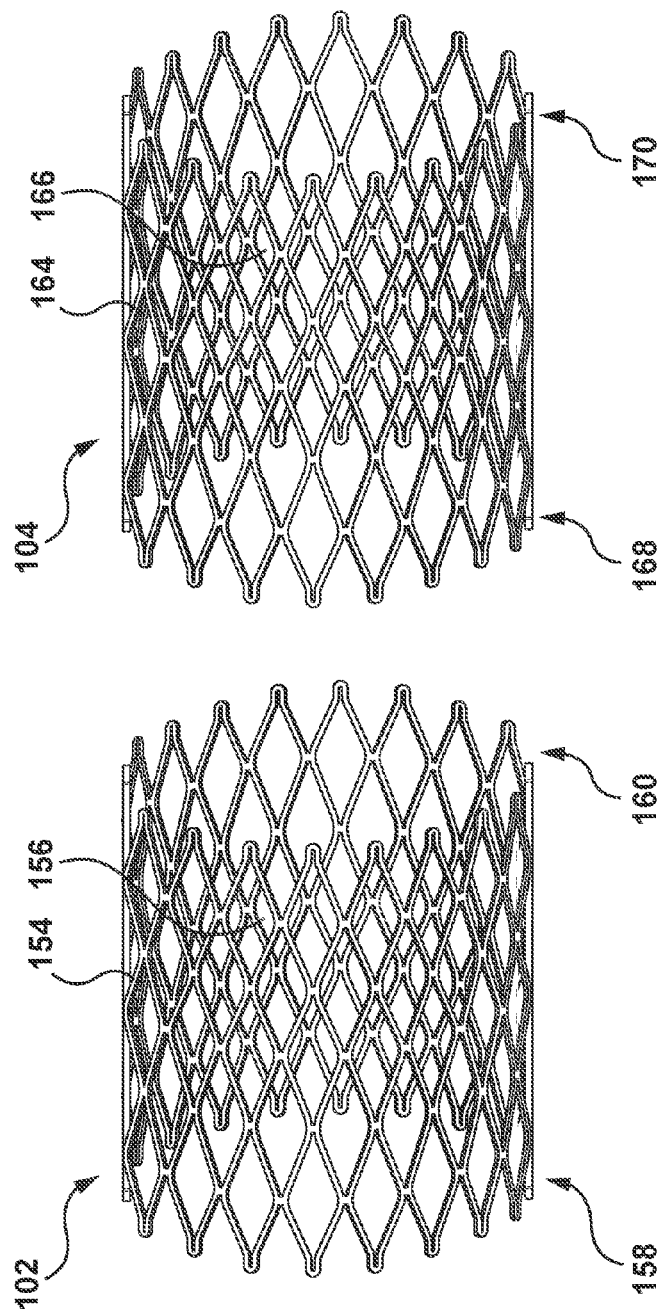
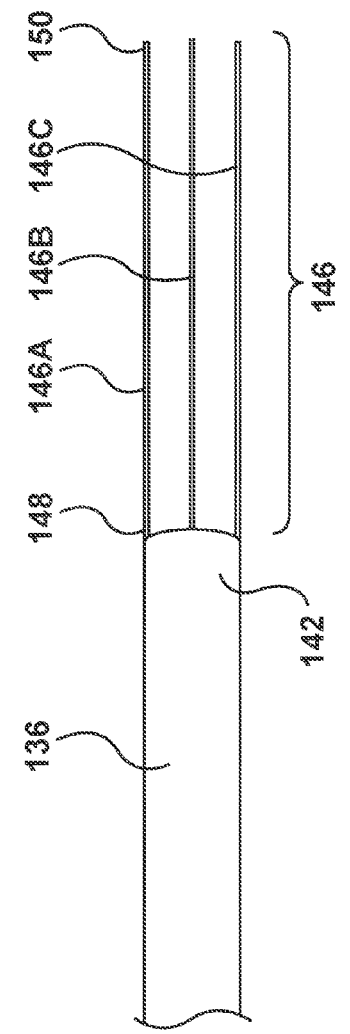
FIG. 2
FIG. 3
FIG. 4

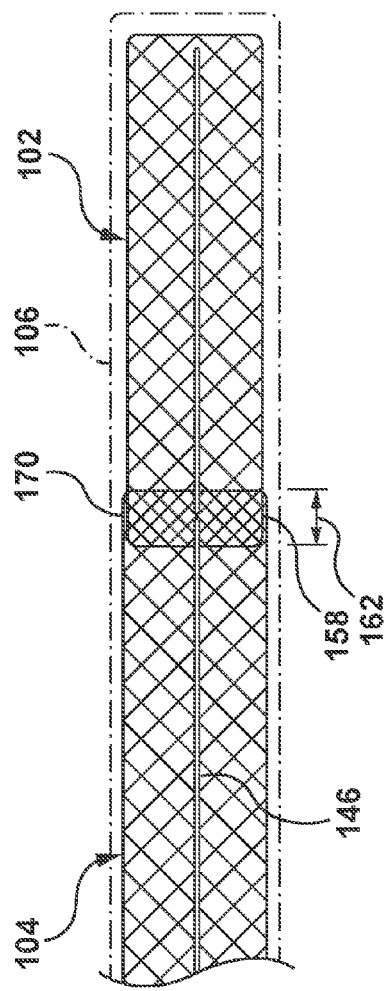
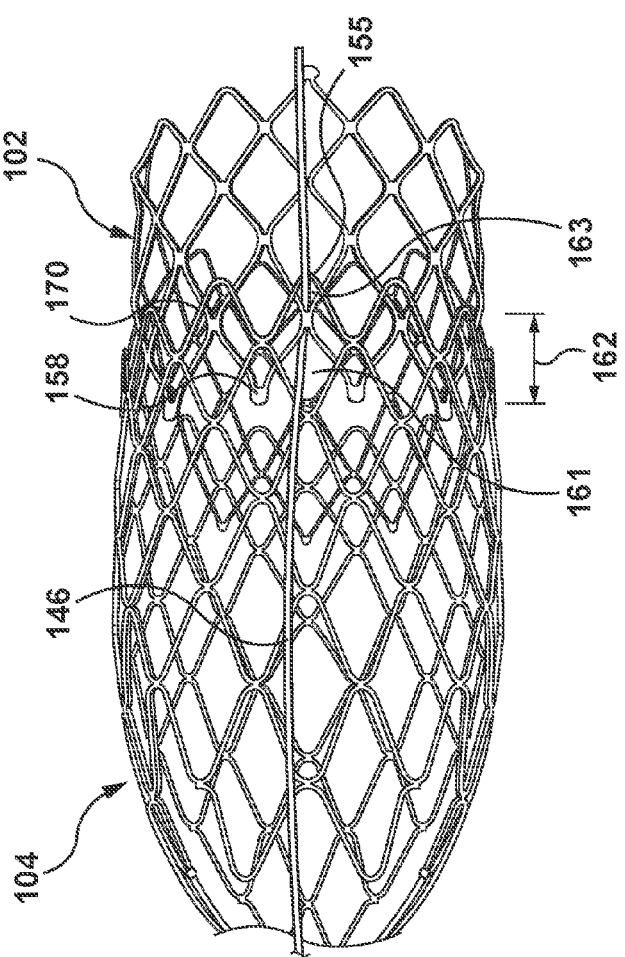
FIG. 5
FIG. 6

DELIVERY SYSTEM HAVING RETRACTABLE WIRES AS A COUPLING MECHANISM AND A DEPLOYMENT MECHANISM FOR A SELF-EXPANDING PROSTHESIS

FIELD OF THE INVENTION

The invention is related in general to a delivery system for a self-expanding prosthesis, and more particularly to a delivery system that utilizes retractable flat wires as a coupling mechanism and a deployment mechanism for a self-expanding prosthesis.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis, in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within an outer sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. Embodiments hereof are directed to a valve prosthesis system having an improved configuration to address one or more of the afore-mentioned complications.

BRIEF SUMMARY OF THE INVENTION

Embodiments hereof relate to a delivery system for transcatheter implantation of a heart valve prosthesis. The delivery system includes an outer sheath component defining a lumen therethrough, an elongate tube having at least two wires longitudinally extending from a distal end thereof, and self-expanding first and second frames disposed in series within a distal portion of the outer sheath component and held in a compressed delivery configuration therein. The elongate tube and the at least two wires being slidably disposed within the lumen of the outer sheath component. In the compressed delivery configuration the at least two wires longitudinally extend along exterior portions of the first and second frames and are woven through adjacent ends of the first and second frames to releasably couple them to each other.

In another embodiment hereof, a delivery system for transcatheter implantation of a heart valve prosthesis includes an outer sheath component defining a lumen therethrough, an elongate tube defining a lumen and having at least two wires longitudinally extending from a distal end thereof, a valve prosthesis having a self-expanding valve frame with a prosthetic valve component secured therein, and a self-expanding docking frame. The elongate tube and the at least two wires being slidably disposed within the lumen of the outer sheath component. The docking frame is disposed distal of the valve prosthesis when each is held in a compressed delivery configuration within a distal portion of the outer sheath component. In the compressed delivery configuration the at least two wires longitudinally extend along exterior portions of the valve frame and the docking frame and are woven through adjacent distal and proximal ends of the valve frame and the docking frame, respectively, to releasably couple them to each other.

Embodiments hereof also relate to a method of implanting a valve prosthesis within a native valve. A delivery system is percutaneously advanced to the native valve. The delivery system includes an outer sheath component defining a lumen therethrough, an elongate tube defining a lumen and having at least two wires longitudinally extending from a distal end thereof, and the elongate tube and the at least two wires being slidably disposed within the lumen of the outer sheath component. The delivery system further includes a valve prosthesis having a self-expanding valve frame with a prosthetic valve component secured therein and a self-expanding docking frame, the docking frame being disposed distal of the valve prosthesis and each frame being held in a compressed delivery configuration within a distal portion of the outer sheath component. The at least two wires longitudinally extend along exterior portions of the valve frame and the docking frame and are woven through adjacent distal and proximal ends of the valve frame and the docking frame, respectively, to releasably couple them to each other. The outer sheath component is proximally retracted to uncover the docking frame and thereby deploy the docking frame to an expanded configuration within the native valve. The outer sheath component is further proximally retracted to uncover the valve frame and thereby deploy the valve frame to an expanded configuration. The at least two wires is proximally retracted from the deployed docking frame to uncouple the deployed docking frame from the deployed valve frame. The deployed valve frame is recaptured into the outer sheath component. The recaptured valve frame is repositioned within the deployed docking frame. The outer sheath component is proximally retracted to uncover the recaptured valve frame and thereby deploy the valve frame to an expanded configuration within the deployed docking frame.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a perspective view of the first frame of FIG. 1, wherein the first frame is removed from the delivery system for sake of illustration only.

FIG. 3 is a perspective view of the second frame of FIG. 1, wherein the second frame is removed from the delivery system for sake of illustration only.

FIG. 4 is a side view of a distal portion of an elongate tube of the delivery system of FIG. 1, wherein the elongate tube includes at least two flat wires longitudinally extending from a distal end thereof and the elongate tube is removed from the delivery system for sake of illustration only.

FIG. 5 is a side sectional view of a distal portion of FIG. 1.

FIG. 6 is a perspective view of the first and second frames and a flat wire of FIG. 1, the first and second frames being shown in their deployed configurations and being shown removed from the delivery system for sake of illustration only, wherein the flat wire is woven through a circumferential overlap region of the first and second frames to releasably couple the frames together.

DETAILED DESCRIPTION OF THE INVENTION

Figure 1:
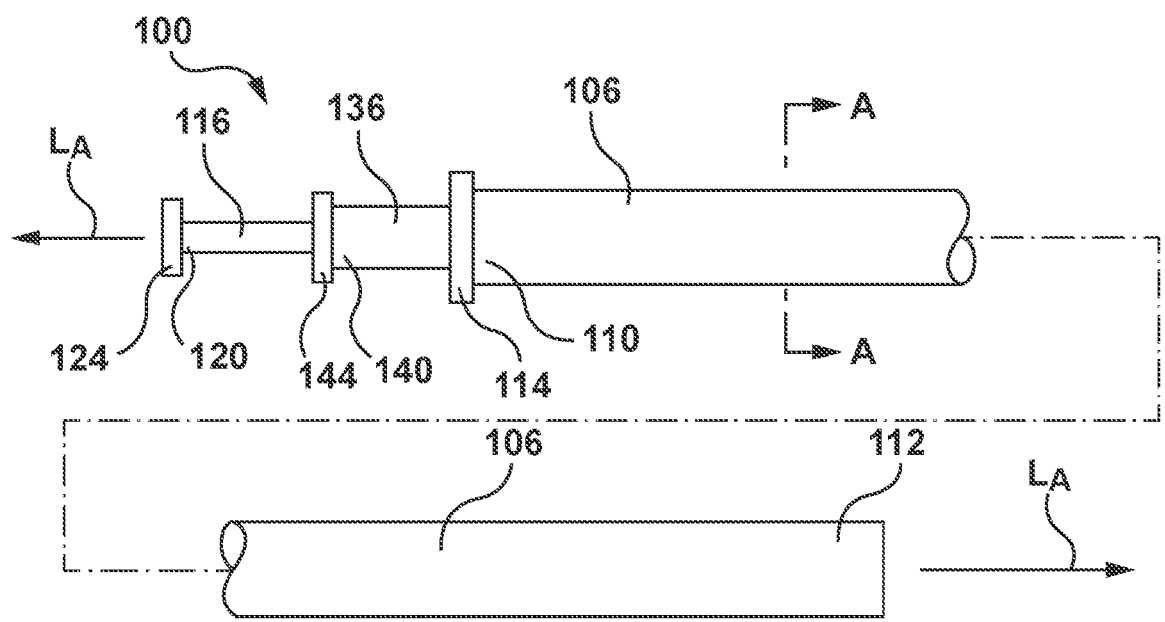
FIG. 1 is a side view of a delivery system according to an embodiment hereof, wherein an outer sheath of the delivery system is in a non-retracted, delivery configuration and is disposed or extends over first and second frames such that the first and second frames are held in a compressed delivery configuration therein.

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of replacement of aortic valves, the prosthetic valves of the invention can also be used in other areas of the body, such as for replacement of a native mitral valve, for replacement of a native pulmonic valve, for replacement of a native tricuspid valve, for use as a venous valve, or for replacement of a failed previously-implanted prosthesis. Furthermore, there is no intention to be bound by any expressed or implied theory presented in the preceding technical field, background, brief summary or the following detailed description.

Embodiments hereof relate to a delivery system for a valve prosthesis that utilizes flexible flat wires as both a coupling mechanism and a deployment mechanism. More particularly, the delivery system includes an outer sheath component defining a lumen therethrough, an elongate tube having at least two flat wires longitudinally extending from a distal end thereof, and self-expanding first and second frames disposed in series within a distal portion of the outer sheath component and held in a compressed delivery configuration therein. As will be explained in more detail herein, a prosthetic valve component may be disposed in the first frame or in the second frame. The elongate tube is slidably disposed within the lumen of the outer sheath component. In the compressed delivery configuration, in which the first and second frames are disposed in series within a distal portion of the outer sheath component, the two flat wires longitudinally extend along exterior portions of the first and second frames and are woven through adjacent ends of the first and second frames to releasably couple them to each other. Proximal retraction of the flat wires from the first and second frames releases at least the first frame from the delivery system such that the flat wires serve as a coupling mechanism for the delivery system. In addition, when the outer sheath component is proximally retracted to uncover the first and second frames for deployment thereof, the flat wires slow the self-expansion of frames to control deployment of the valve prosthesis such that the flat wires also serve as a deployment mechanism for the delivery system.

Figure 1A:
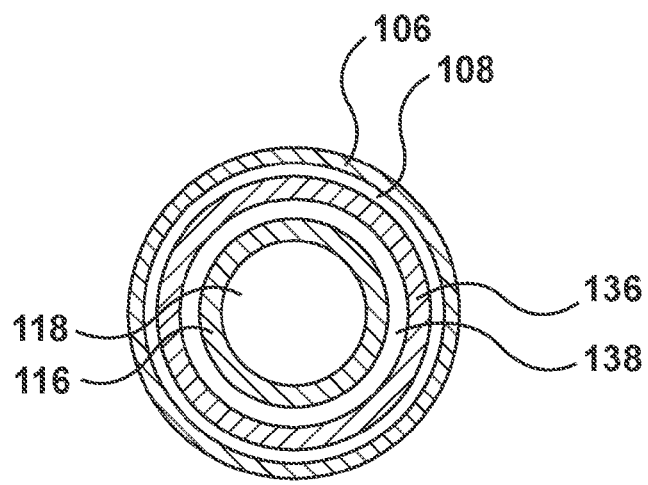
FIG. 1A is a cross-sectional view taken along line A-A of FIG. 1.

More particularly, with reference to the side view of FIG. 1 and the cross-sectional view of FIG. 1A taken along line A-A of FIG. 1, delivery system 100 includes an outer sheath component or cover 106, an elongate tube 136 slidingly disposed within outer sheath component 106, and an inner shaft 116 slidingly disposed within elongate tube 136. Elongate tube 136 has at least two flat or ribbon wires 146 longitudinally extending from a distal end 142 thereof which are utilized as both a coupling mechanism and a deployment mechanism for delivery system 100. Self-expanding first and second frames 102, 104, respectively, are disposed or mounted at a distal portion of delivery system 100. First and second frames 102, 104 are disposed in series such that they are adjacent to each other or side-by-side in a longitudinal direction, i.e., along a longitudinal axis $L_A$ of delivery system 100. First frame 102 is disposed distal to second frame 104, and thus first frame 102 may be referred to herein as distal frame 102 and second frame 104 may be referred to herein as proximal frame 104.

As shown in the perspective views of FIGS. 2 and 3, first and second frames 102, 104 are shown in their expanded or deployed configurations and removed from delivery system 100 for illustrative purposes only. First and second frames 102, 104 each include a self-expanding scaffold 154, 164, respectively, that returns to an expanded deployed state from a compressed or constricted delivery state. In this embodiment, self-expanding scaffolds 154, 164 are tubular components having proximal ends or segments 158, 168, respectively, and distal ends or segments 160, 170, respectively, with diamond-shaped openings 156, 166, respectively, that may be formed by a laser-cut manufacturing method and/or another conventional stent/scaffold forming method as would be understood by one of ordinary skill in the art. However, it will be understood by one of ordinary skill in the art that the illustrated configurations of first and second frames 102, 104 are exemplary and self-expanding scaffolds 154, 164 may have alternative patterns or configurations. For example, in another embodiment (not shown), self-expanding scaffolds 154, 164 may include one or more sinusoidal patterned rings coupled to each other to form a tubular component. Further, depending upon application thereof and as will be described in more detail herein, the first and/or second frame may each have distinct configurations and/or include an additional element that aids in fixing or anchoring the self-expanding frame within native valve anatomy.

With reference to FIG. 1 and FIG. 1A, the main components of delivery system 100 will now be described in more detail. Outer sheath component 106 is an elongate shaft or tubular component that defines a lumen 108 extending from a proximal end 110 to a distal end 112 thereof. Outer sheath component 106 is movable in an axial direction along and relative to inner shaft 116 and extends to a proximal portion of the delivery system where it may be controlled via an actuator, such as a handle 114 to selectively expand first and second frames 102, 104. Handle 114 may be a push-pull actuator that is attached or connected to proximal end 110 of outer sheath component 106. Alternatively, the actuator may be a rotatable knob (not shown) that is attached or connected to proximal end 110 of outer sheath component 106 such that when the knob is rotated, outer sheath component 106 is retracted in a proximal direction to expand the first and second frames. Alternatively, the actuator may use a combination of rotation and sliding to retract outer sheath component 106, as described, for example, in U.S. Pat. No. 7,419,501 to Shiu et al., U.S. Patent Publication No. 2011/0257718 to Argentine, U.S. Patent Publication No. 2011/0270371 to Argentine, and U.S. Patent Publication No. 2011/0270372 to Argentine, each of which is incorporated by reference herein. Thus, when the actuator is operated, i.e., manually turned or pulled, outer sheath component 106 is proximally retracted over inner shaft 116 in a proximal direction. Outer sheath component 106 may be constructed of any suitable flexible polymeric material, including but not limited to polyethylene terephalate (PET), nylon, polyethylene, PEBAX, or combinations thereof, either blended or co-extruded.

Elongate tube 136 having flat wires 146 longitudinally extending from distal end 142 thereof is an elongate shaft or tubular component that defines a lumen 138 extending from a proximal end 140 to distal end 142 thereof. Elongate tube 136 is slidingly disposed within lumen 108 of outer sheath component 106. Elongate tube 136 is movable in an axial direction along and relative to inner shaft 116 and extends to a proximal portion of the delivery system where it may be controlled via an actuator, such as a handle 144 to selectively proximally retract flat wires 146. Handle 144 may be a push-pull actuator, a rotatable knob, or an actuator that uses a combination of rotation and sliding to retract the shaft component as described herein with respect to handle 114 and is attached or connected to proximal end 140 of elongate tube 136. Elongate tube 136 may be constructed of any suitable flexible polymeric material, including but not limited to polyethylene terephalate (PET), nylon, polyethylene, PEBAX, or combinations thereof, either blended or co-extruded. A side view of a distal portion of elongate tube 136 is shown in FIG. 4. Elongate tube 136 includes a total of three flat wires 146A, 146B, 146C, collectively referred to herein as flat wires 146, which longitudinally extend from distal end 42 of elongate tube 136. More particularly, proximal ends 148 of each flat wire 146 is attached or fixed to distal end 142 of elongate tube 136 and distal ends 150 are not attached or free ends such that flat wires 146 may be woven through first and second frames 102, 104 to couple them to the delivery system as will be explained in more detail herein. Although shown with three flat wires 146, it will be understood by those of ordinary skill in the art that a greater or smaller number of flat wires may be used depending upon the size or diameter of first and second frames 102, 104. Further, although flat wires 146 preferably having an oval, oblong, or rectangular cross-section and a flat or flattened profile in order to minimize the delivery profile thereof, the wires may alternatively have a circular or other shape cross-section as will be understood by those of ordinary skill in the art. The length of flat wires 146 depend upon the length of first and second frames 102, 104 as flat wires 146 are configured to extend at least approximately the full length of the first and second frames 102, 104 when in the compressed delivery configuration. Flat wires 146 may be formed from Nitinol, stainless steel, PEEK, or similar materials.

Inner shaft 116 is an elongate shaft or tubular component that defines a lumen 118 extending from a proximal end 120 to a distal end 122 thereof. Lumen 118 of inner shaft 116 is sized to slidingly receive a plunger (shown in FIG. 19) with a dilator tip (shown in FIG. 19) at a distal end thereof. The plunger defines a guidewire lumen such that delivery system 100, including the plunger extending therethrough, may be advanced over a guidewire (shown in FIG. 19) to assist in tracking the delivery system to the target site within the vasculature. Inner shaft 116 is slidingly disposed within lumen 138 of elongate tube 136. As will be described in more detail herein, distal end 122 of inner shaft 116 is coupled to proximal end 168 of second or proximal frame 104. In an embodiment hereof, distal end 122 of inner shaft 116 is permanently attached to the proximal end of second or proximal frame 104 such that proximal frame 104 is a permanent component of the delivery system. In another embodiment hereof, distal end 122 of inner shaft 116 is releasably coupled to the proximal end of second or proximal frame 104 such that proximal frame 104 may be selectively detached from the delivery system and thus is not a permanent component of the delivery system. Inner shaft 116 is movable in an axial direction along and relative to outer sheath component 106 and extends to a proximal portion of the delivery system where it may be controlled via an actuator, such as a handle 124 to selectively proximally retract second or proximal frame 104. Handle 124 may be a push-pull actuator, a rotatable knob, or an actuator that uses a combination of rotation and sliding to retract the shaft component as described herein with respect to handle 114 and is attached or connected to proximal end 120 of inner shaft 116. Inner shaft 116 may be constructed of any suitable flexible polymeric material, including but not limited to polyethylene terephalate (PET), nylon, polyethylene, PEBAX, or combinations thereof, either blended or co-extruded.

In order to couple first and second frames 102, 104 to delivery system 100, distal end 122 of inner shaft 116 is coupled to proximal end 168 of second or proximal frame 104 as stated above and second or proximal frame 104 is releasably coupled to proximal end 158 of first or distal frame 102. In the compressed delivery configuration of FIG. 1, outer sheath component 106 is in a non-retracted, delivery configuration and is disposed or extends over first and second frames 102, 104 such that the first and second frames are held or retained in a compressed delivery configuration therein. As best shown in the sectional view of FIG. 5, when in the compressed delivery configuration, first and second frames 102, 104 are mounted in series with proximal end 158 of first or distal frame 102 overlapping distal end 170 of second or proximal frame 104 to provide a circumferential overlap region 162 therebetween. More particularly, distal end or segment 170 of second or proximal frame 104 is disposed or nested within proximal end or segment 158 of first or distal frame 102 such that proximal end 158 of first or distal frame 102 overlays or covers distal end 170 of second or proximal frame 104 at circumferential overlap region 162. However, as will be understood by those of ordinary skill in the art, proximal end 158 of first or distal frame 102 may alternatively be disposed within distal end 170 of second or proximal frame 104 at circumferential overlap region 162.

With additional reference to the enlarged view of FIG. 6, flat wires 146 are woven through overlapping openings 156, 166 of first and second frames 102, 104 along circumferential overlap region 162 in order to releasably couple first and second frames 102, 104 together. The enlarged view of FIG. 6 illustrates only a single flat wire 146 for clarity. In the circumferential overlap region 162, each flat wire 146 is threaded under or woven through a respective distalmost crown 155 of second or proximal frame 104. More particularly, flat wire 146 extends along an outer surface of second or proximal frame 104. Distal to proximal end 158 of first or distal frame 102 and within circumferential overlap region 162, flat wire 146 passes through a first set 161 of overlapping openings 156, 166 within circumferential overlap region 162 such that flat wire 146 is disposed within first or distal frame 102. Proximal to distal end 170 of second or proximal frame 104 and within circumferential overlap region 162, flat wire 146 passes through a second set 163 of overlapping openings 156, 166 within circumferential overlap region 162 such that flat wire 146 is disposed and extends along an outer surface of first or distal frame 102 for the remaining length thereof. As a result, once all flat wires 146 are positioned in a similar manner, first or distal frame 102 is releasably coupled to second or proximal frame 104 as well as to delivery system 100 (via second or proximal frame) via flat wires 146.

Figure 7:
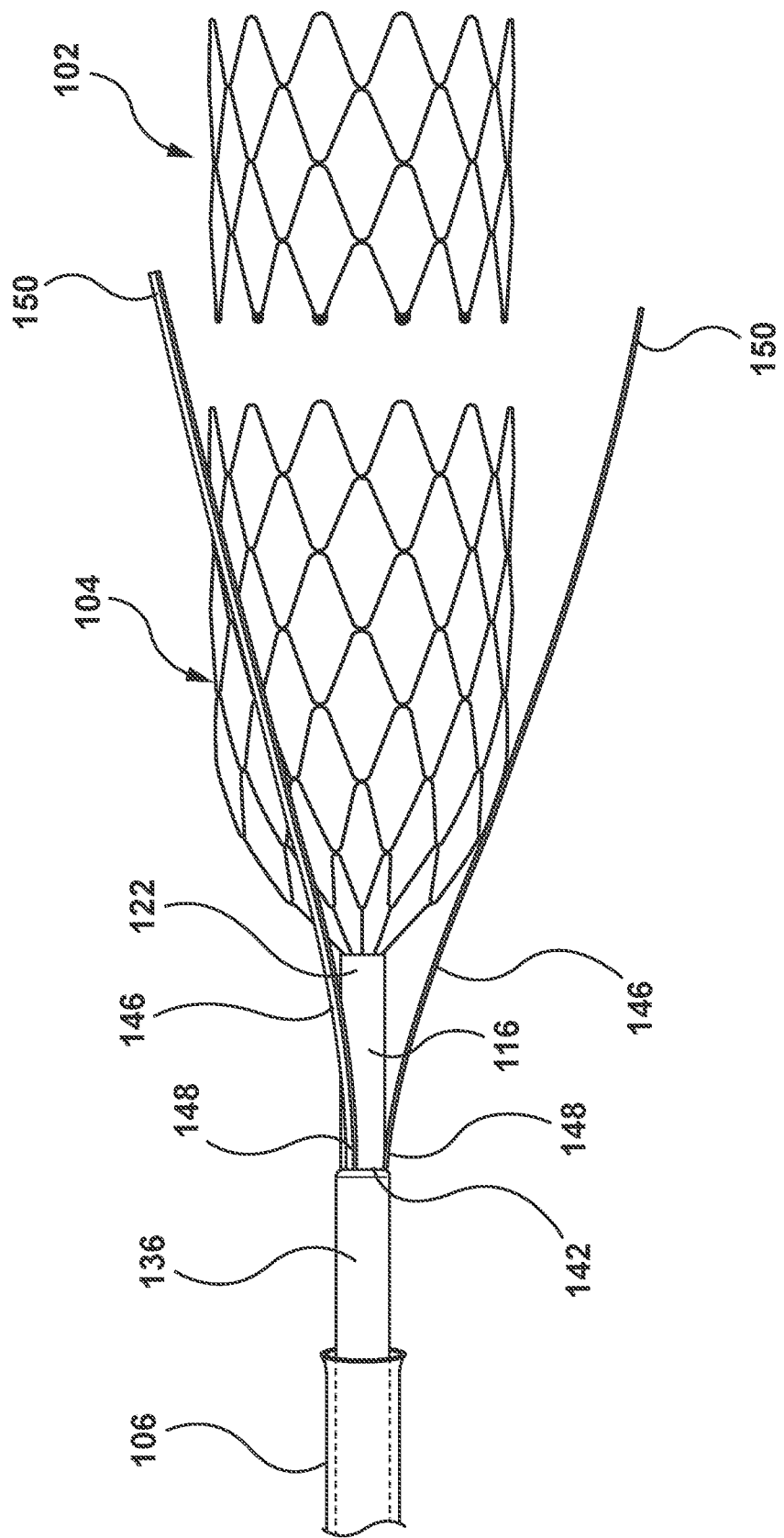
FIG. 7 is a side view of the delivery system of FIG. 1, wherein the outer sheath of the delivery system is in retracted configuration, the first and second frames are in their expanded or deployed configurations, and the flat wires are shown radially extending beyond the first and second frames for illustrative purposes only.

As shown in FIG. 7, proximal retraction of flat wires 146 from circumferential overlap region 162 releases at least first or distal frame 102 from delivery system 100. When flat wires 146 are proximally retracted such that they are no longer woven through overlapping openings 156, 166 of first and second frames 102, 104 along circumferential overlap region 162, first and second frames 102, 104 are no longer coupled together via the flat wires. Second or proximal frame 104 (which is coupled to inner shaft 116) may be proximally retracted to separate from first or distal frame 102, as shown in FIG. 7, such that first or distal frame 102 does not contact proximal frame 104 and is decoupled from delivery system 100. In FIG. 7, flat wires 146 are shown radially extending beyond proximal frame 104 for illustrative purposes only. When in use, elongate tube 136 having flat wires 146 longitudinally extending therefrom would be proximally retracted such that flat wires 146 were at least partially housed within outer sheath component 106.

Figure 8:
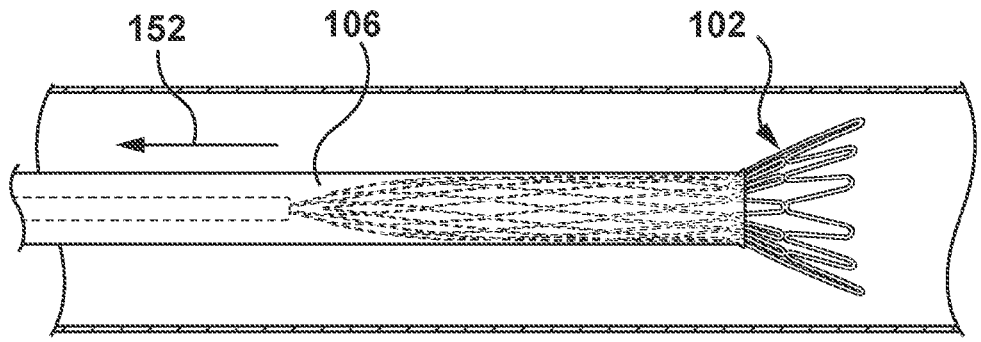
FIG. 8 illustrates a step for deploying the first and second frames and decoupling at least the first or distal frame from the delivery system of FIG. 1, wherein the step includes retraction of the outer sheath of the delivery system.

More particularly, FIGS. 8-14 illustrate the steps for deploying first and second frames 102, 104 and decoupling at least first or distal frame 102 from delivery system 100. In FIG. 8, outer sheath component 106 is being proximally retracted as shown by directional arrow 152 and first or distal frame 102 is partially deployed. Although hidden from view in this figure, second or proximal frame 104 is compressed and restrained within outer sheath component 106 and flat wires 146 are woven through overlapping openings 156, 166 of first and second frames 102, 104 along circumferential overlap region 162 in order to releasably couple first and second frames 102, 104 together as described with respect to FIG. 6. When outer sheath component 106 is proximally retracted to uncover first or distal frame 102, flat wires 146 slow the self-expansion of the first frame to control deployment thereof. Stated another way, the expansion rate of distal frame 102 is slower with flat wires 146 disposed thereover as compared to the expansion rate of distal frame 102 without flat wires 146 disposed thereover. Slower expansion results in more controlled and predictable deployment of distal frame 102.

Figure 9:
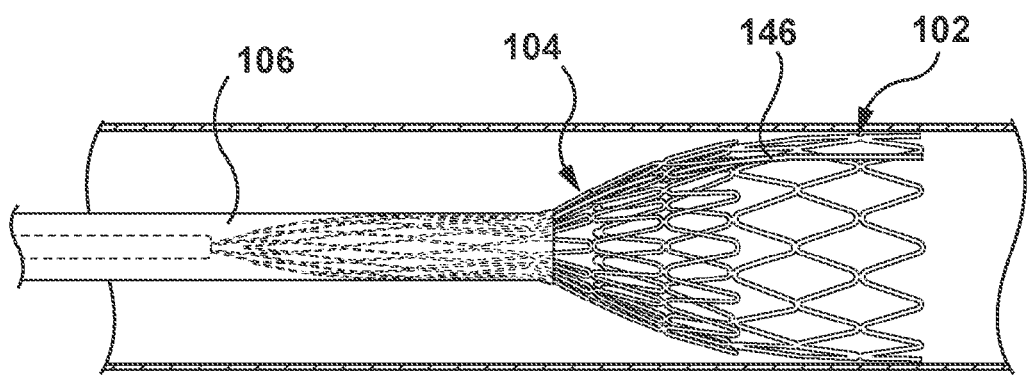
FIG. 9 illustrates a step for deploying the first and second frames and decoupling at least the first or distal frame from the delivery system of FIG. 1, wherein the step includes further retraction of the outer sheath of the delivery system to expose or uncover the first frame.

Retraction of outer sheath component 106 continues until first or distal frame 102 is completely outside of outer sheath component 106 and thus fully expanded as shown in FIG. 9. In FIG. 9, second or proximal frame 104 is partially deployed or expanded with outer sheath component 106 still disposed over a proximal portion thereof. At this stage of deployment, flat wires 146 are still woven through overlapping openings 156, 166 of first and second frames 102, 104 along circumferential overlap region 162 in order to releasably couple first and second frames 102, 104 together as described with respect to FIG. 6. When outer sheath component 106 is proximally retracted to uncover second or proximal frame 102, flat wires 146 slow the self-expansion of the second frame to control deployment thereof. When each of the first and second frames is at least partially expanded distal of outer sheath component 106 while remaining coupled to each other by flat wires 146, first and second frames 102, 104 are recapturable by outer sheath component 106. More particularly, if repositioning of first frame 102 is desired, outer sheath component 106 may be distally advanced over flat wires 146 and first and second frames 102, 104 in order to recapture first and second frames 102, 104 within outer sheath component 106. When recaptured, first and second frames 102, 104 resume their compressed, delivery configuration described above with respect to FIG. 5 and first frame 102 may be repositioned.

Figure 10:
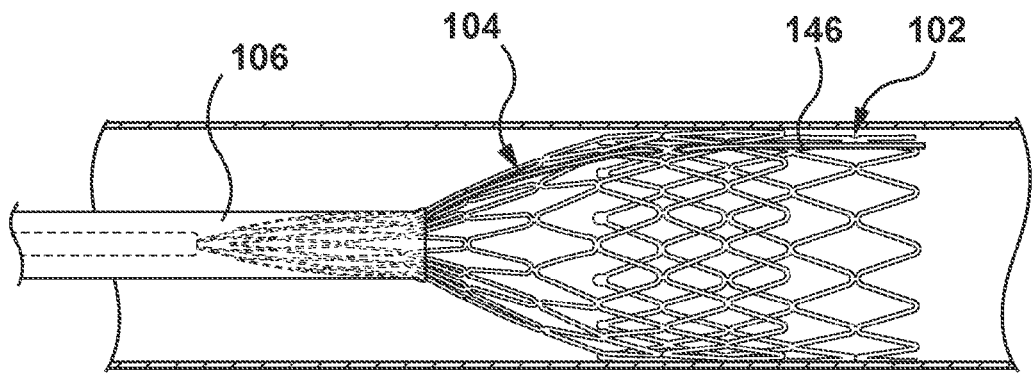
FIG. 10 illustrates a step for deploying the first and second frames and decoupling at least the first or distal frame from the delivery system of FIG. 1, wherein the step includes further retraction of the outer sheath of the delivery system to also expose or uncover the second frame.

Retraction of outer sheath component 106 continues until both first and second frames 102, 104 are completely outside of outer sheath component 106 and thus fully expanded as shown in FIG. 10. At this stage of deployment, flat wires 146 are still woven through overlapping openings 156, 166 of first and second frames 102, 104 along circumferential overlap region 162 in order to releasably couple first and second frames 102, 104 together as described with respect to FIG. 6, and first and second frames 102, 104 are still recapturable by outer sheath component 106 as described above.

Figure 11:
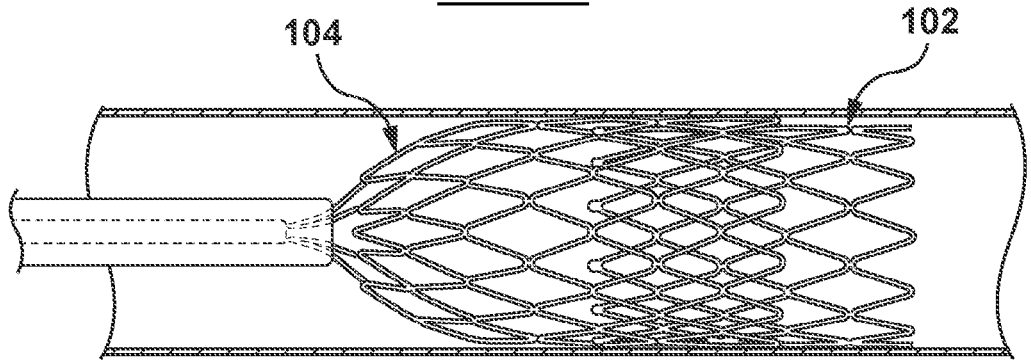
FIG. 11 illustrates a step for deploying the first and second frames and decoupling at least the first or distal frame from the delivery system of FIG. 1, wherein the step includes retraction of the flat wires to decouple the first frame from the second frame.

Once first frame 102 is positioned as desired (i.e., repositioning is no longer desired and recapturability is thus no longer required), flat wires 146 are proximally retracted in order to decouple first or distal frame 102 from second or proximal frame 104 and delivery system 100 as shown in FIG. 11. More particularly, elongate tube 136 having flat wires 146 attached thereto is proximally retracted relative to inner shaft 116 until distal ends 150 of flat wires 146 are positioned proximal to second or proximal frame 104. Distal ends 150 are preferably rounded and flat wires 146 are sufficiently flexible in order to avoid potential tissue damage during retraction thereof.

Figure 12:
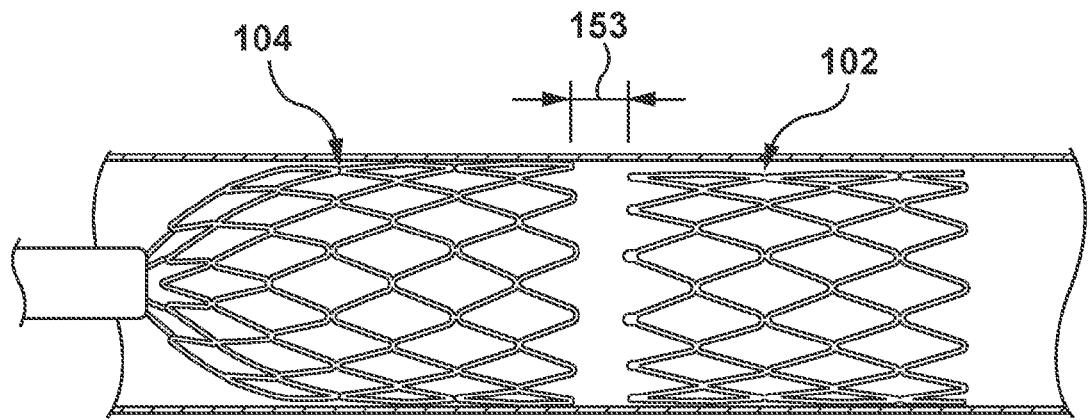
FIG. 12 illustrates a step for deploying the first and second frames and decoupling at least the first or distal frame from the delivery system of FIG. 1, wherein the step includes retraction of second frame to separate the second frame from the first frame.

After first or distal frame 102 is decoupled from delivery system 100, second or proximal frame 104 is proximally retracted in order to separate first and second frames 102, 104. More particularly, inner shaft 116 having second frame 104 coupled thereto is proximally retracted relative to elongate tube 136 until a gap or space 153 spans between first and second frames 102, 104 as shown in FIG. 12. As described above, prior to separation thereof, distal end 170 of second or proximal frame 104 is disposed within proximal end 158 of first or distal frame 102. As such, at this stage of deployment, first or distal frame 102 is expanded into apposition with the vessel wall and thus remains in position when second or proximal frame 104 is proximally retracted and detached therefrom.

Figure 13:
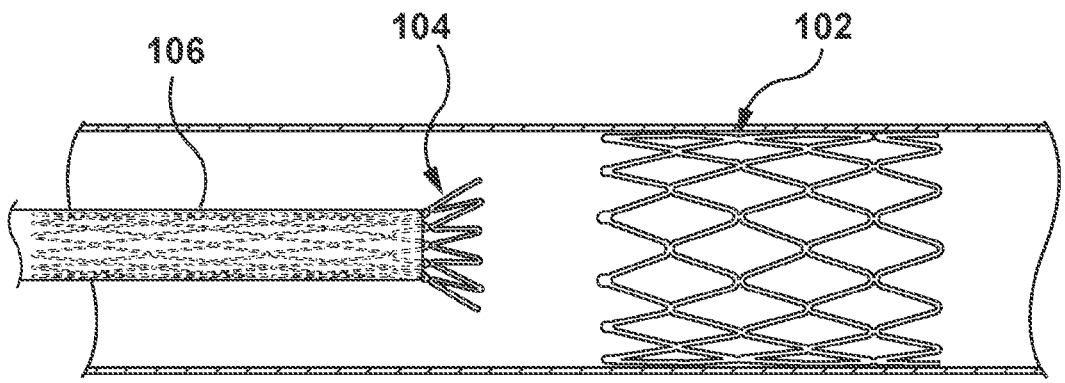
FIG. 13 illustrates a step for deploying the first and second frames and decoupling at least the first or distal frame from the delivery system of FIG. 1, wherein the step includes retraction of second frame into the outer sheath for recapture.
Figure 14:
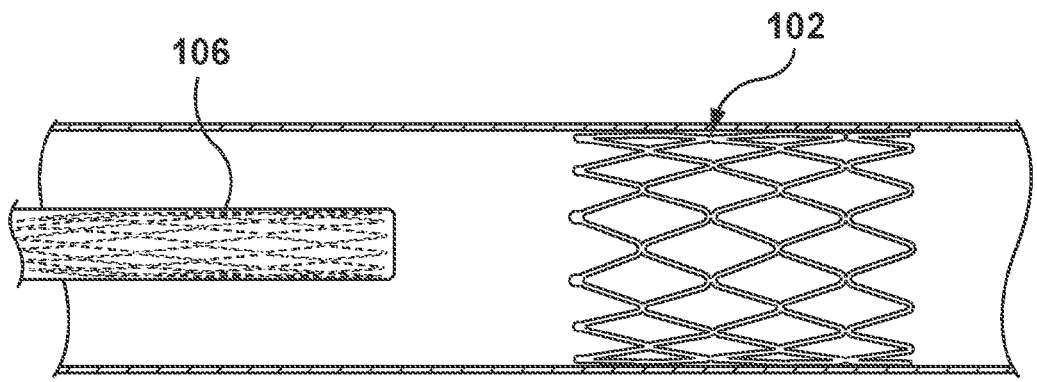
FIG. 14 illustrates a step for deploying the first and second frames and decoupling at least the first or distal frame from the delivery system of FIG. 1, wherein the step includes further retraction of second frame into the outer sheath for recapture.

After first and second frames 102, 104 are separated from each other, inner shaft 116 is further proximally retracted relative to outer sheath component 106 in order to recapture second or proximal frame 104. As inner shaft 116 is pulled into outer sheath component 106, if not previously retracted into outer sheath component 106, flat wires 146 are also further proximally retracted relative to outer sheath component 106 in order to be recaptured with proximal frame 104. In FIG. 13, second or proximal frame 104 is shown partially recaptured with outer sheath component 106 disposed over a proximal portion thereof. In FIG. 14, second or proximal frame 104 is shown fully recaptured within outer sheath component 106. Once fully recaptured, second or proximal frame 104 may be removed or may be repositioned for deployment thereof. More particularly, when proximal frame 104 is a permanent component of the delivery system according to an embodiment hereof as will be described in more detail herein with respect to FIGS. 15-23, proximal frame 104 is ready for removal once it is decoupled from distal frame 102 and recaptured by outer sheath component 106. In another embodiment hereof, when proximal frame 104 detachable from the delivery system and is not a permanent component of the delivery system as will be described in more detail herein with respect to FIGS. 24-33, proximal frame 104 is ready to be positioned for deployment thereof once it is decoupled from distal frame 102 and recaptured by outer sheath component 106. Although recapture of second or proximal frame 104 is described via proximal retraction of inner shaft 116, it would be understood by those of ordinary skill in the art that the required relative movement between outer sheath component 106 and inner shaft 116 may be accomplished via distal advancement of outer sheath component 106.

FIGS. 15-23 illustrate an embodiment hereof in which the first or distal frame is the scaffold of a valve prosthesis that is delivered by delivery system 100 and the second or proximal frame is a permanent component of delivery system 100. Flat wires 146 and the proximal frame couple the valve prosthesis to delivery system 100 and flat wires 146 are utilized in deployment of the valve prosthesis. In this embodiment, a first or distal frame 1602 is the scaffold of a valve prosthesis, and thus first or distal frame 1602 may be referred to herein as valve frame 1602 and a second or proximal frame 1504 may be referred to herein as delivery frame 1504.

Figure 15:
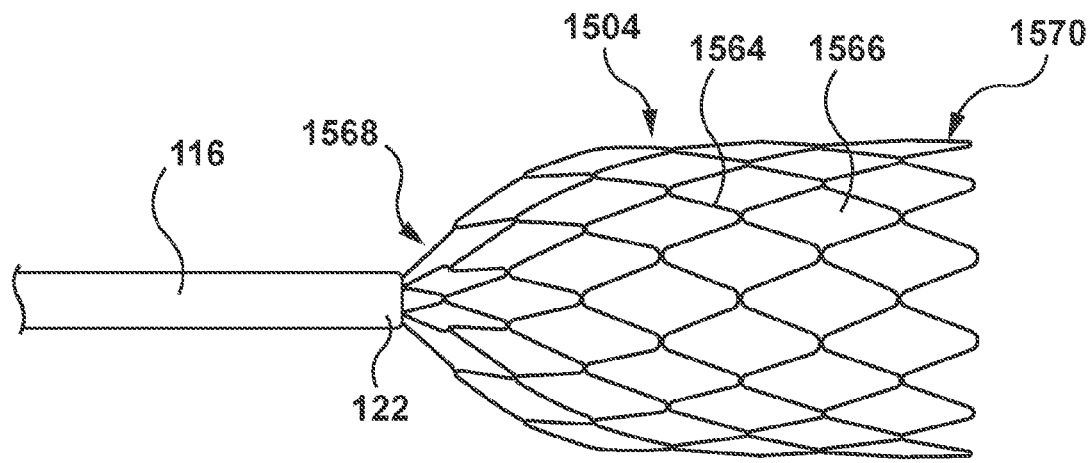
FIG. 15 is a side view of a distal portion of an inner shaft of the delivery system of FIG. 1 according to an embodiment hereof, wherein a second or delivery frame is permanently attached or secured to a distal end of the inner shaft to be slidable therewith.
Figure 16:
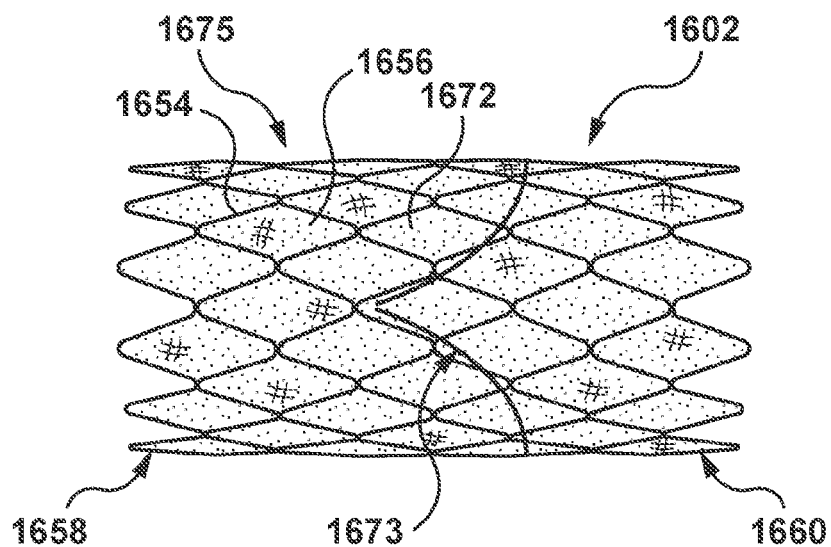
FIG. 16 is a side view of a valve prosthesis to be used with the delivery frame of FIG. 15, the valve prosthesis being shown in its expanded configuration and being removed from the delivery system for illustrative purposes only, wherein the valve prosthesis includes a first or valve frame and a prosthetic valve component disposed therein.

FIG. 15 illustrates a distal portion of a distal portion of inner shaft 116 having delivery frame 1504 attached thereto, with inner shaft 116 and delivery frame 1504 removed from the remainder of the delivery system for illustrative purposes only. In this embodiment hereof, distal end 122 of inner shaft 116 is permanently attached or secured to a proximal end of delivery frame 1504 to be slidable therewith. Distal end 122 of inner shaft 116 may be permanently attached or secured to a proximal end of delivery frame 1504 via welding, use or more one or adhesives, bonding, or via other mechanical methods known in the art. Delivery frame 1504 is shown in its expanded or deployed configuration. FIG. 16 illustrates valve frame 1602 in its expanded or deployed configuration, removed from the delivery system for illustrative purposes only. Similar to first and second frames 102, 104 described above, valve and delivery frames 1602, 1504 each include a self-expanding scaffold 1654, 1564, respectively, that returns to an expanded deployed state from a compressed or constricted delivery state. In this embodiment, self-expanding scaffolds 1654, 1564 are tubular components having proximal ends or segments 1658, 1568, respectively, and distal ends or segments 1660, 1570, respectively, with diamond-shaped openings 1656, 1566, respectively, that may be formed by a laser-cut manufacturing method and/or another conventional stent/scaffold forming method as would be understood by one of ordinary skill in the art.

Figure 17:
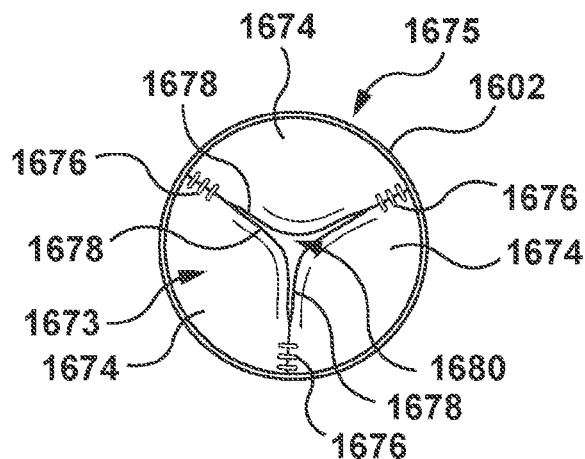
FIG. 17 is an end view of the valve prosthesis of FIG. 16.

In this embodiment, valve frame 1602 includes a prosthetic valve component 1673 disposed within and secured to scaffold 1654. Prosthetic valve component 1673 includes at least two valve leaflets 1674 disposed within and secured to scaffold 1654. Prosthetic valve component 1673 is capable of blocking flow in one direction to regulate flow therethrough via valve leaflets 1674 that may form a bicuspid or tricuspid replacement valve. FIG. 17 is an end view of prosthetic valve component 1673 taken from the second or outflow end thereof. FIG. 17 illustrates an exemplary tricuspid valve having three leaflets 1674, although a bicuspid leaflet configuration may alternatively be used in embodiments hereof. More particularly, if prosthetic valve component 1673 is configured for placement within a native valve having three leaflets such as the aortic, tricuspid, or pulmonary valves, prosthetic valve component 1673 includes three valve leaflets 1674 although the valve prosthesis is not required to have the same number of leaflets as the native valve. If prosthetic valve component 1673 is configured for placement within a native valve having two leaflets such as the mitral valve, prosthetic valve component 1673 includes two or three valve leaflets 1674. Valve leaflets 1674 are sutured or otherwise securely and sealingly attached (i.e., via suitable biocompatible adhesive) to the inner surface of scaffold 1654. Adjoining pairs of leaflets are attached to one another at their lateral ends to form commissures 1676, with free edges 1678 of the leaflets forming coaptation edges that meet in area of coaptation 1680. Valve frame 1602 and prosthetic valve component 1673 may be collectively referred to herein as a valve prosthesis 1675.

Leaflets 1674 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 1674 include DACRON® commercially available from Invista North America S.A.R.L. of Wilmington, Del., other cloth materials, nylon blends, and polymeric materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Valve frame 1602 may also include a tubular body or graft material 1672 attached to an inner or outer surface of scaffold 1654. It will be understood by one of ordinary skill in the art that at least some portions of scaffold 1654 are not covered by the graft material such that flat wires 146 may be woven or passed therethrough. Graft material 1672 may be formed from any suitable biocompatible material, for example and not limited to, a low-porosity woven or knit polyester, DACRON®, polytetrafluoroethylene (PTFE), polyurethane, silicone, or other suitable materials. Graft material 1672 is thin-walled so that valve frame 1602 may be compressed into a small diameter, yet is capable of acting as a strong, leak-resistant fluid conduit when expanded to a cylindrical tubular form. In one embodiment, graft material 1672 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material could also be a natural material such as pericardium or another membranous tissue such as intestinal submucosa.

Figure 18:
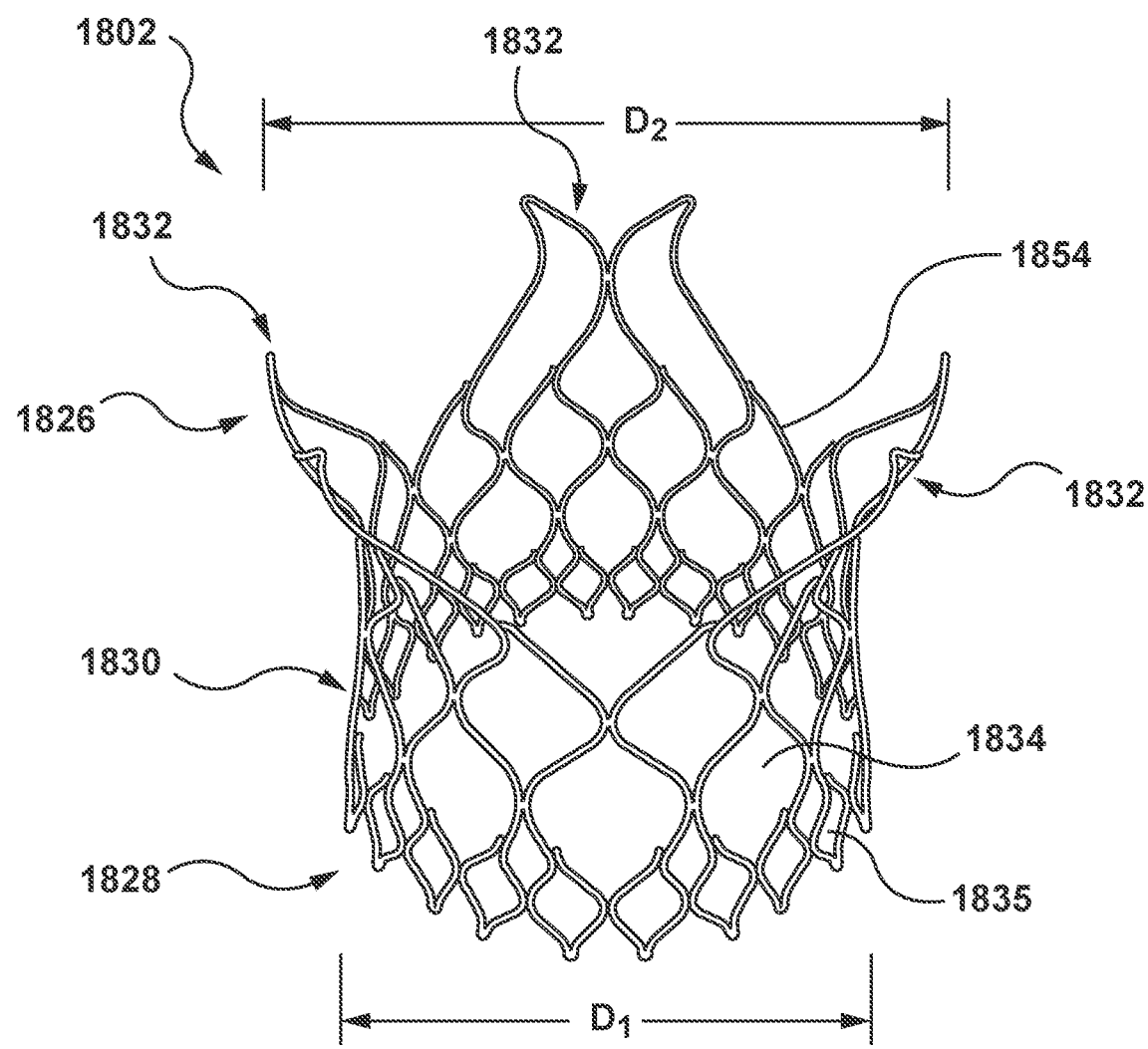
FIG. 18 is a perspective view of a valve frame according to another embodiment hereof.

It will be understood by one of ordinary skill in the art that the illustrated configuration of scaffold 1654 is exemplary and scaffold 1654 may have an alternative pattern or configuration. For example, in another embodiment shown in FIG. 18, a scaffold 1854 of a valve frame 1802 is shown. Scaffold 1854 is configured to easily recapture into delivery system 100 and controlled release thereof is improved due to the relatively smaller amount of material at the outflow end thereof. More particularly, scaffold 1854 includes an outflow end 1826, an inflow end 1828, and an intermediate portion 1830 extending therebetween. Openings 1834 of intermediate portion 1830 are relatively larger in size than openings 1835 of inflow end 1828. Outflow end 1826 includes three circumferentially spaced-apart extensions 1832 that are bulged or flared compared to intermediate portion 1830 and inflow end 1828. Outflow end 1826 thus has a relatively smaller amount of scaffold material compared to the amount of scaffold material at inflow end 1828. Due to the configuration of outflow end 1832, valve frame 1802 is relatively easier to recapture via outer sheath component 106 of delivery system 100. As shown in FIG. 18, outflow end 1826 has a diameter $D_2$ which is larger than a diameter $D_1$ of opposing inflow end 1828. The sizes of diameters $D_1$ and $D_2$ may vary according to a particular patient's anatomy and/or the intended native valve for replacement.

Figure 19:
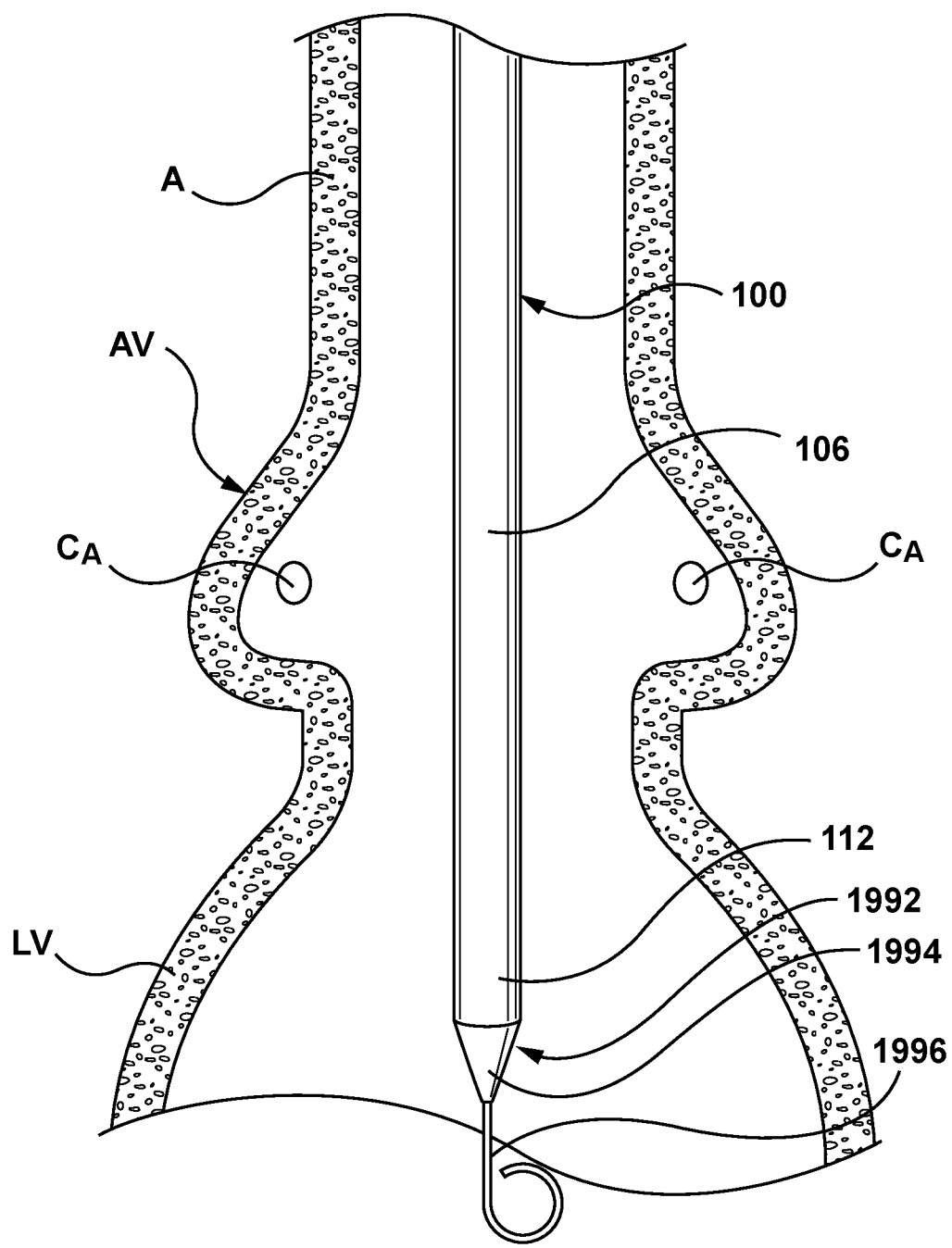
FIG. 19 illustrates a step for implanting the valve prosthesis of FIG. 16, wherein the step includes delivery of the delivery system with the outer sheath thereof in a non-retracted, delivery configuration such that the valve and delivery frames are held in a compressed delivery configuration therein.

FIGS. 19-23 illustrate an exemplary method of implanting the above-described valve frame 1602 within a native valve according to an embodiment hereof. As described above with respect to FIG. 5, when in the compressed delivery configuration, valve and delivery frames 1602, 1504 are mounted in series with the proximal end of distal or valve frame 1602 overlapping the distal end of proximal or delivery frame 1504 at an overlap region. Valve and delivery frames 1602, 1504 are held in a radially compressed configuration via outer sheath component 106. The radially compressed configurations of valve and delivery frames 1602, 1504 are suitable for percutaneous delivery within a vasculature. As shown in FIG. 19, in accordance with techniques known in the field of interventional cardiology and/or interventional radiology, delivery system 100 having a plunger 1992 disposed there-through is transluminally advanced in a retrograde approach over a guidewire 1996 through the vasculature to the treatment site, which in this instance is a target diseased native aortic valve AV that extends between a patient's left ventricle LV and a patient's aorta A. The coronary arteries $C_A$ are also shown on the sectional view of FIG. 19. Plunger 1992 includes a dilator tip 1994 at a distal end thereof. Delivery of delivery system 100 to the native aortic valve AV may be accomplished via a percutaneous transfemoral approach or may be positioned within the desired area of the heart via different delivery methods known in the art for accessing heart valves. During delivery, i.e., while being tracked over guidewire 1996, valve and delivery frames 1602, 1504 remain compressed within outer sheath component 106 of delivery system 100. Delivery system 100 is advanced until distal end 112 of outer sheath component 106 is distal to the native aortic valve AV and disposed within the left ventricle LV as shown in FIG. 19. In an embodiment, delivery system 100 is advanced approximately 5 mm into the left ventricle LV.

Figure 20:
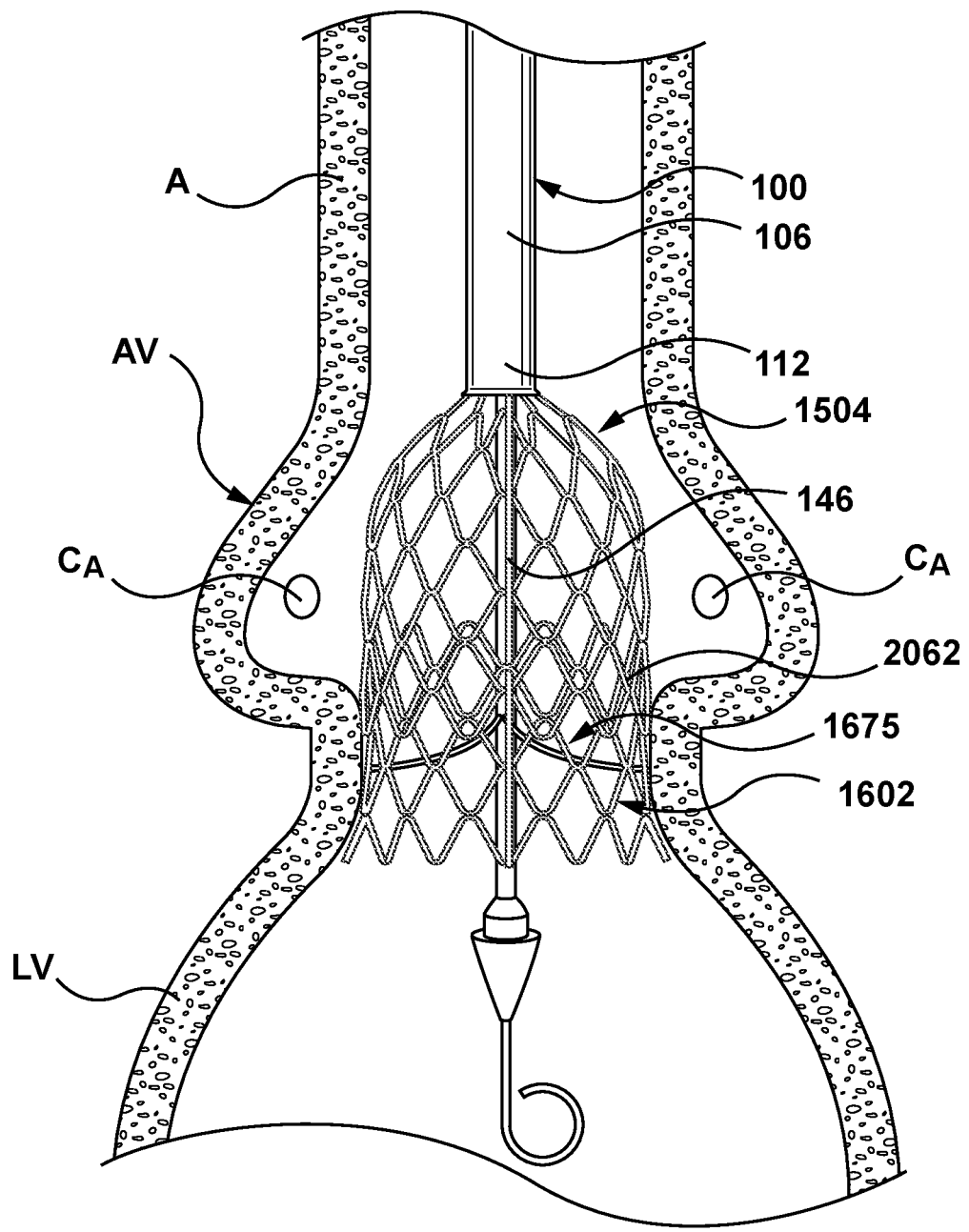
FIG. 20 illustrates a step for implanting the valve prosthesis of FIG. 16, wherein the step includes proximal retraction of the outer sheath to expand or deploy the valve and delivery frames.

Once delivery system 100 is positioned as desired, outer sheath component 106 is proximally retracted in order to radially expand or deploy valve and delivery frames 1602, 1504 as shown in FIG. 20. At this stage of deployment, flat wires 146 are woven through overlapping openings 1656, 1566 of valve and delivery frames 1602, 1504 along a circumferential overlap region 2062 in order to releasably couple valve and delivery frames 1602, 1504 together as described with respect to FIG. 6. The graft material of valve frame 1602 is not shown in FIGS. 20-23 for sake of clarity. When outer sheath component 106 is proximally retracted to uncover valve and delivery frames 1602, 1504, flat wires 146 slow the self-expansion of valve and delivery frames 1602, 1504 to control deployment thereof. When valve frame 1602 is at least partially expanded distal of outer sheath component 106 while remaining coupled to delivery frame 1504 by flat wires 146, valve prosthesis 1675 is recapturable by outer sheath component 106 being distally advanced over flat wires 146. More particularly, if repositioning of valve frame 1602 is desired, outer sheath component 106 may be distally advanced over flat wires 146 in order to recapture valve and delivery frames 1602, 1504 within outer sheath component 106. When recaptured, valve and delivery frames 1602, 1504 resume their compressed, delivery configuration described above with respect to FIG. 5 and valve frame 1602 may be repositioned.

Figure 21:
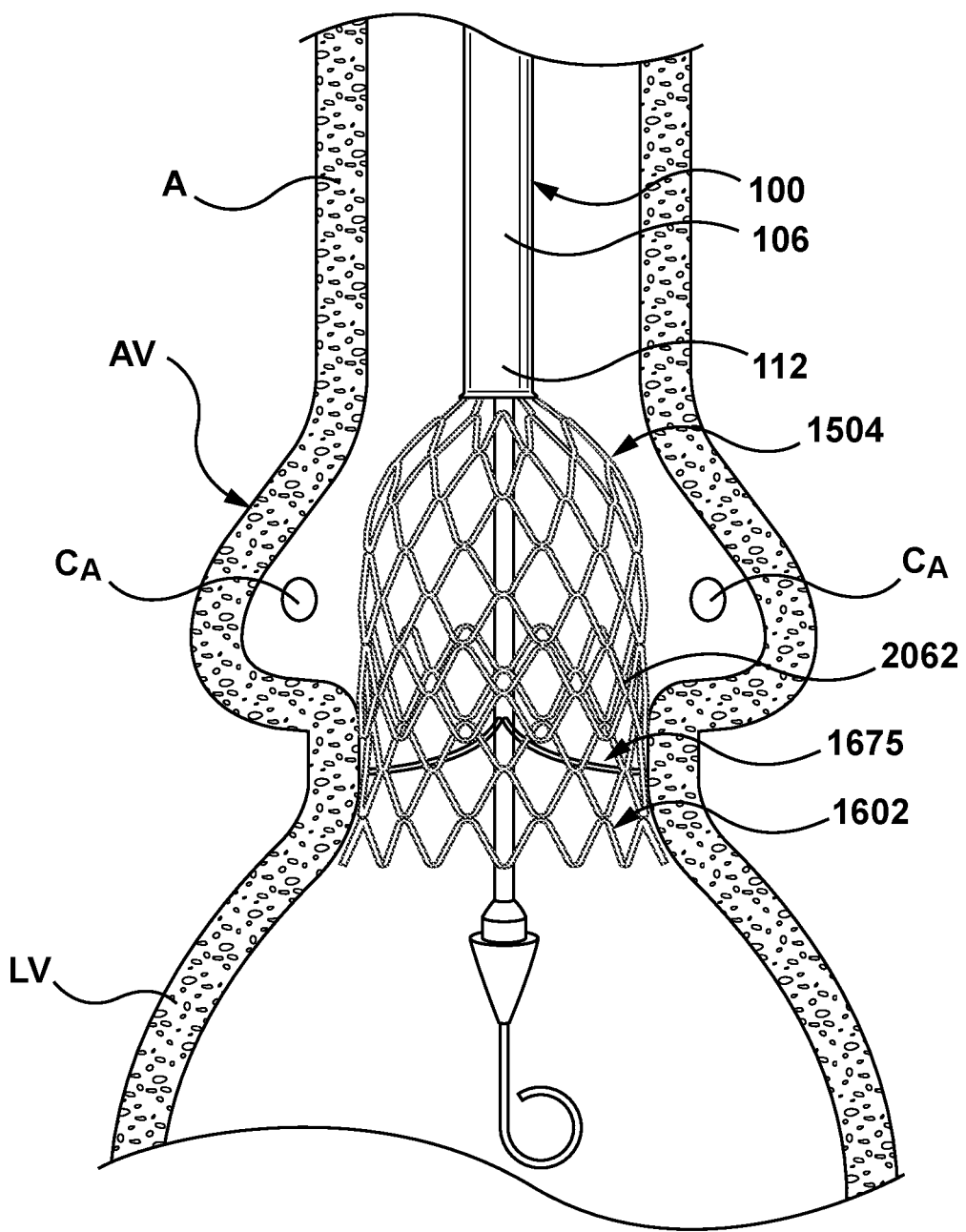
FIG. 21 illustrates a step for implanting the valve prosthesis of FIG. 16, wherein the step includes proximal retraction of the flat wires to decouple the valve and delivery frames.

Once valve prosthesis 1675 is positioned as desired (i.e., repositioning is no longer desired and recapturability is thus no longer required), flat wires 146 are proximally retracted in order to decouple valve frame 1602 from delivery frame 1504 and delivery system 100 as shown in FIG. 21. More particularly, elongate tube 136 having flat wires 146 attached thereto is proximally retracted relative to inner shaft 116 until distal ends 150 of flat wires 146 are positioned proximal to delivery frame 1504. Proximal retraction of flat wires 146 from valve frame 1602 releases valve prosthesis 1675 from delivery system 100.

Figure 22:
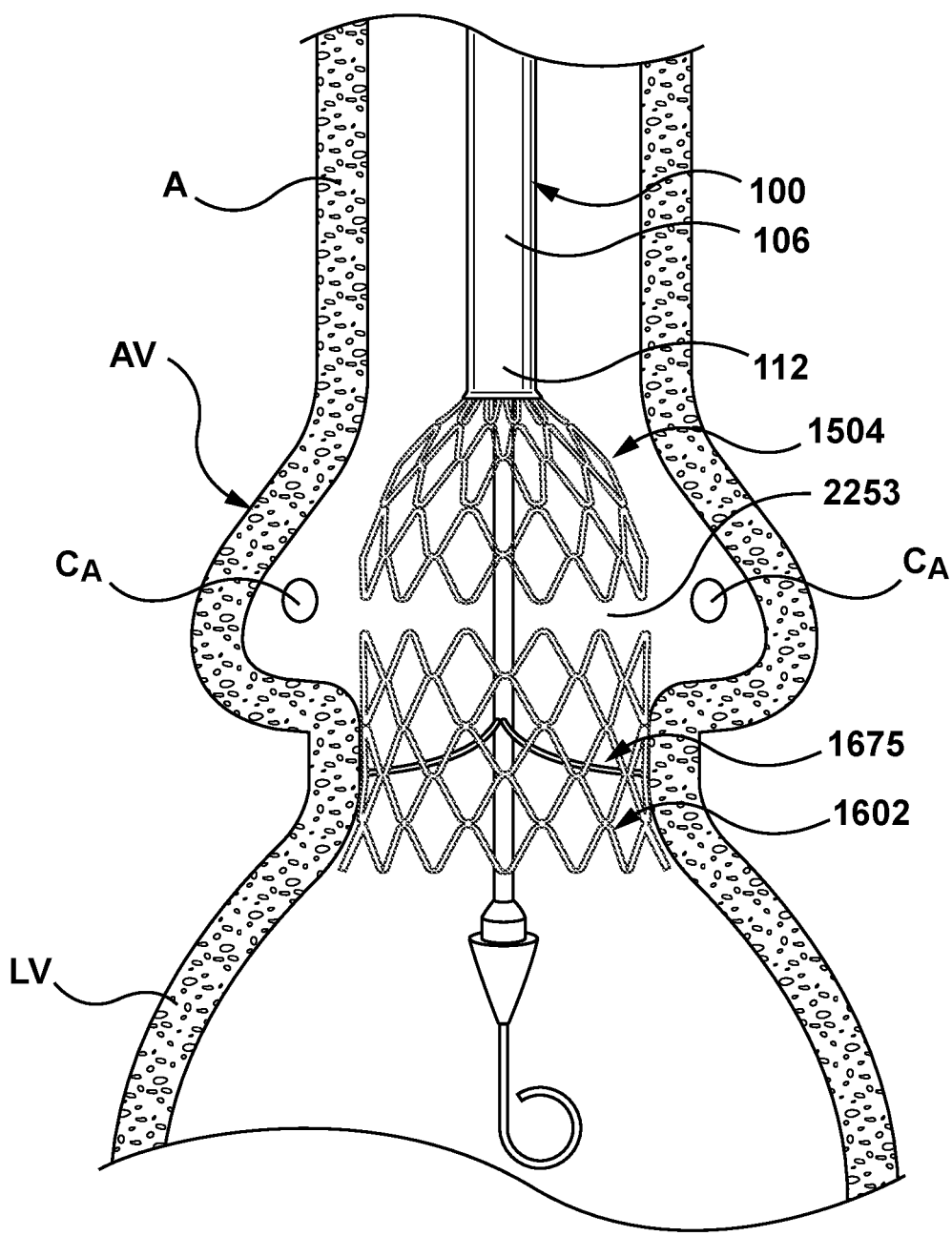
FIG. 22 illustrates a step for implanting the valve prosthesis of FIG. 16, wherein the step includes proximal retraction of the delivery frame to separate the delivery frame from the valve frame.

After valve prosthesis 1675 is decoupled from delivery system 100, delivery frame 1504 is proximally retracted in order to separate valve and delivery frames 1602, 1504. More particularly, inner shaft 116 having delivery frame 1504 attached thereto is proximally retracted relative to elongate tube 136 until a gap or space 2253 spans between valve and delivery frames 1602, 1504 as shown in FIG. 22. As described above, prior to separation thereof, the distal end of delivery frame 1504 is disposed within the proximal end of valve frame 1602. As such, at this stage of deployment, valve frame 1602 is expanded into apposition with the native heart valve, and thus remains in position when delivery frame 1504 is proximally retracted and detached therefrom.

Figure 23:
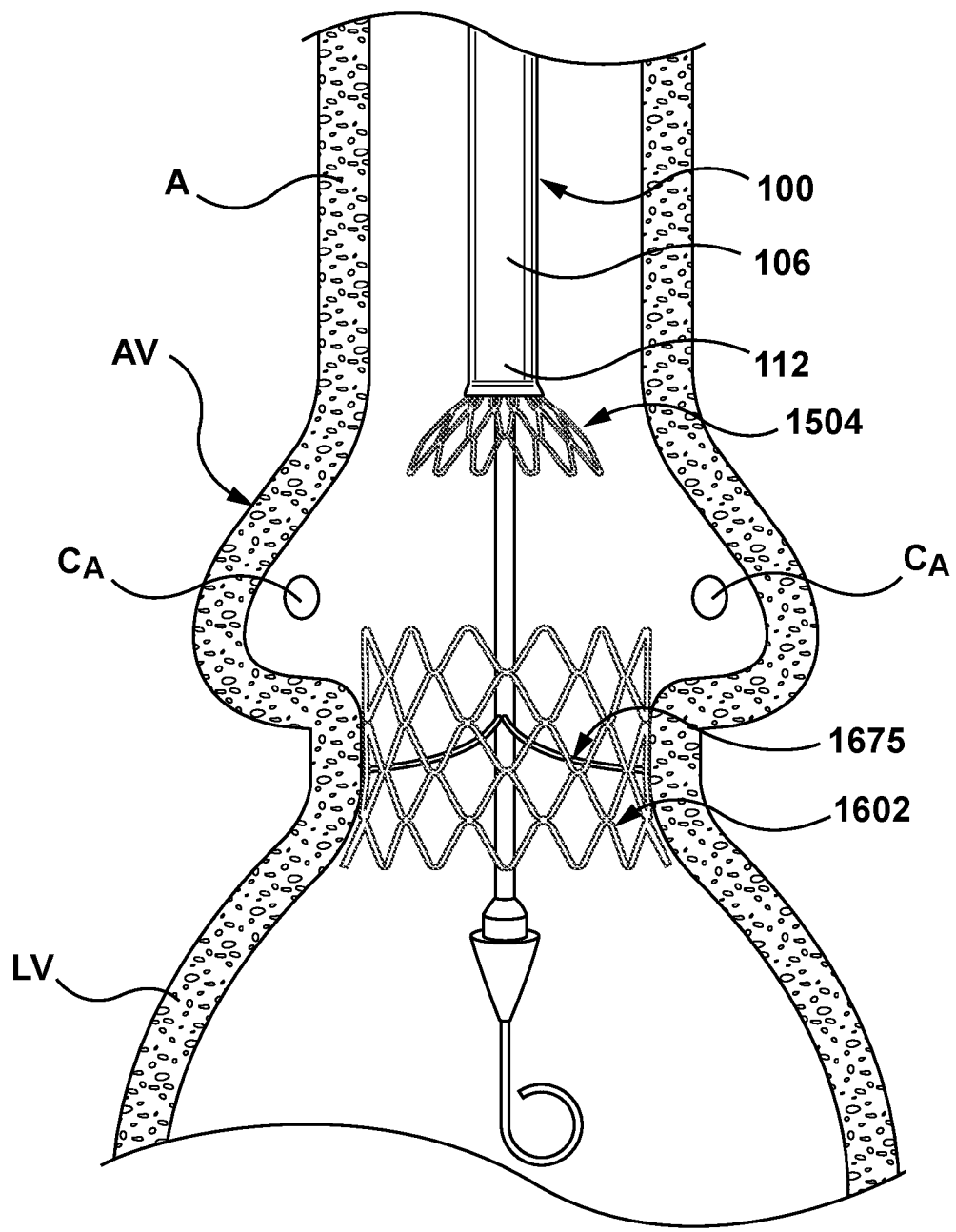
FIG. 23 illustrates a step for implanting the valve prosthesis of FIG. 16, wherein the step includes proximal retraction of the delivery frame into the outer sheath to recapture the delivery frame for removal thereof.

After valve and delivery frames 1602, 1504 are separated from each other, inner shaft 116 is further proximally retracted relative to outer sheath component 106 in order to recapture delivery frame 1504 as shown in FIG. 23. As inner shaft 116 is pulled into outer sheath component 106, if not previously retracted into outer sheath component 106, flat wires 146 are also further proximally retracted relative to outer sheath component 106 in order to be recaptured with proximal frame 104. In FIG. 23, delivery frame 1504 is shown partially recaptured with outer sheath component 106 disposed over a proximal portion thereof. Once delivery frame 1504 is fully recaptured within outer sheath component 106, delivery system 100 including delivery frame 1504 attached thereto may be removed.

Advantageously, valve frame 1602 may be a relatively short valve frame that does not block or extend over the coronary arteries $C_A$ as shown in FIGS. 20-23. In an embodiment, valve frame 1602 has a length of 35 mm or less. Delivery frame 1504 permits the relatively short valve frame 1602 to be deployed similar to a longer frame via the use of flat wires 146 that attach valve frame 1602 to delivery system 100. More particularly, during the deployment of a self-expanding frame from an outer sheath, the radial force of the frame as it is partially deployed creates a force in the distal direction. When a relatively short frame is released, the frame may move in the direction of the outer sheath retraction and may cant at the implantation site, which is unintentional slanting or tilting of the frame. If a valve prosthesis is not circumferentially centered relative to the native annulus, the deployed valve prosthesis may dislodge from the implantation site and/or undesirable paravalvular leakage and/or regurgitation may occur. Thus, it is important that the valve prosthesis be accurately located relative to the native annulus prior to full deployment of the prosthesis. With relatively longer frames, canting is mitigated by the fact that much of the frame gradually deploys into contact with tissue at the implantation site which provides anchoring and control during deployment before the longer frame is fully released from the outer sheath. Since delivery frame 1504 and valve frame 1602 are deployed while coupled together, delivery frame 1504 and valve frame 1602 collectively deploy similar to a longer frame and thus reduce the chance of valve frame 1602 canting. Delivery frame 1504 and flat wires 146 enable the short valve frame 1602 to be gradually released or deployed, and valve frame 1602 remains coupled to delivery system 100 during deployment thereof so that valve frame 1602 deploys into contact with tissue at the implantation site prior to release from the delivery system.

FIGS. 24-33 illustrate an embodiment hereof in which the first or distal frame is a docking frame that is configured to receive the second or proximal frame having a prosthetic valve component secured therein. Thus, in this embodiment, the second or proximal frame is not a permanent component of delivery system 100 but rather distal end 122 of inner shaft 116 is releasably coupled to the proximal end of the second or proximal frame such that the proximal frame may be selectively detached from the delivery system. In this embodiment, a second or proximal frame 2404 is the scaffold of a valve prosthesis, and thus second or proximal frame 2404 may be referred to herein as valve frame 2404 and a first or distal frame 2602 may be referred to herein as docking frame 2602. Flat wires 146 of delivery system 100 couple docking and valve frames 2602, 2404 together and are utilized in deployment of both of the frames as will be described in more detail herein. Delivery system 100 thus is utilized for a two-stage deployment in which docking frame 2602 and valve frame 2404 are concurrently delivered or advanced to the target native valve or treatment site but docking frame 2602 is deployed prior to valve frame 2404. Docking frame 2602 is configured to be released from and implanted by delivery system 100 at an implantation site, i.e., within one of a native heart valve or previously implanted prosthetic valve, and thereafter valve frame 2404 with the prosthetic valve component secured therein is configured to be released from and implanted by delivery system 100 within docking frame 2602.

Figure 24:
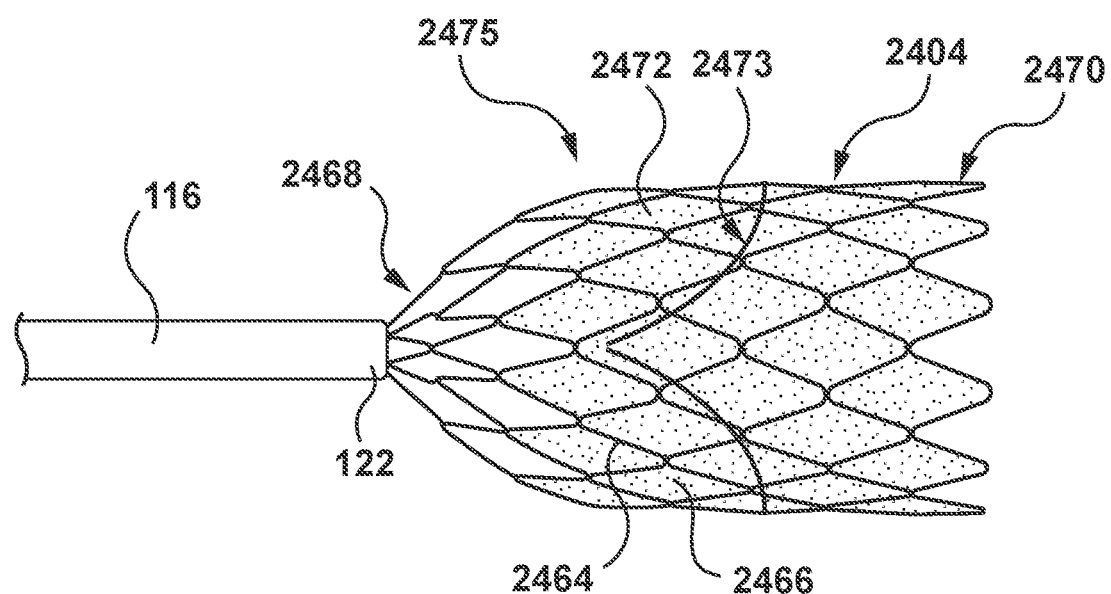
FIG. 24 is a side view of a distal portion of an inner shaft of the delivery system of FIG. 1 according to an embodiment hereof, wherein a valve prosthesis is releasably secured to a distal end of the inner shaft to be slidable therewith, and the valve prosthesis includes a first or valve frame and a prosthetic valve component disposed therein.
Figure 25:
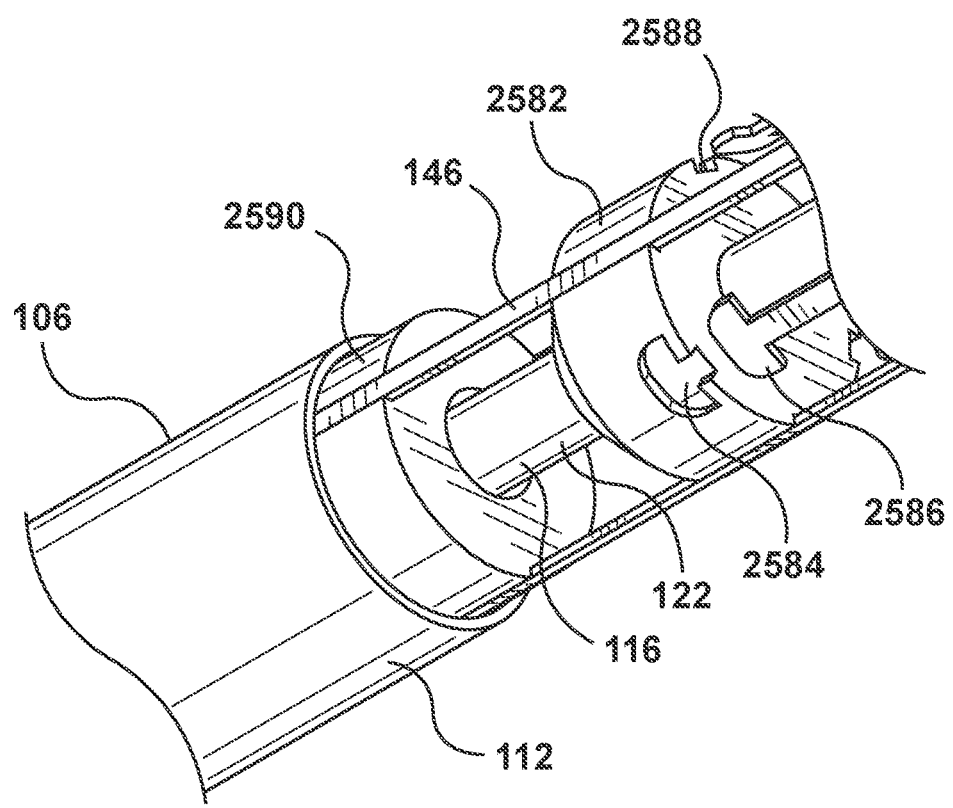
FIG. 25 is a perspective view of the releasable connection between the valve prosthesis and the inner shaft.

More particularly, FIG. 24 illustrates a distal portion of inner shaft 116 having valve frame 2404 attached thereto, with inner shaft 116 and valve frame 2404 removed from the remainder of the delivery system for illustrative purposes only. In this embodiment hereof, distal end 122 of inner shaft 116 is releasably attached or secured to a proximal end of valve frame 2404 to be slidable therewith. More particularly, with reference to FIG. 25, distal end 122 of inner shaft 116 includes a distal hub 2582 which functions to releasably couple the proximal end of valve frame 2404 to inner shaft 116. Distal hub 2582 includes recesses 2584 while the proximal end of valve frame 2404 includes paddles 2586 proximally extending from the proximal end of the valve frame. Paddles 2586 are configured to mate or be received within recesses 2584 of distal hub 2582 to couple valve frame 2404 to inner shaft 116. However, when it is desired to deploy valve frame 2404 as described herein, self-expansion of valve frame 2404 causes paddles 2586 to release or exit out of recesses 2584, thereby decoupling valve frame 2404 from inner shaft 116. As shown in FIG. 25, distal hub 2582 may also include longitudinal grooves 2588 configured to allow passage and sliding of flat wires 146 longitudinally extending from elongate tube 136 thereover. In the embodiment of FIG. 25, distal end 142 of elongate tube 136 includes a distal hub 2590 for attachment or securement of flat wires 146 to elongate tube 136. Flat wires 146 may be glued, welded, molded, or otherwise mechanically attached to distal hub 2590, and distal hub 2590 similarly may be glued, welded, molded, or otherwise mechanically attached to distal end 142 of elongate tube 136. Although not shown, it will be understood by one of ordinary skill in the art that a distal hub similar to distal hub 2590 may be incorporated into any embodiment described herein for attaching flat wires 146 to distal end 142 of elongate tube 136.

Figure 26:
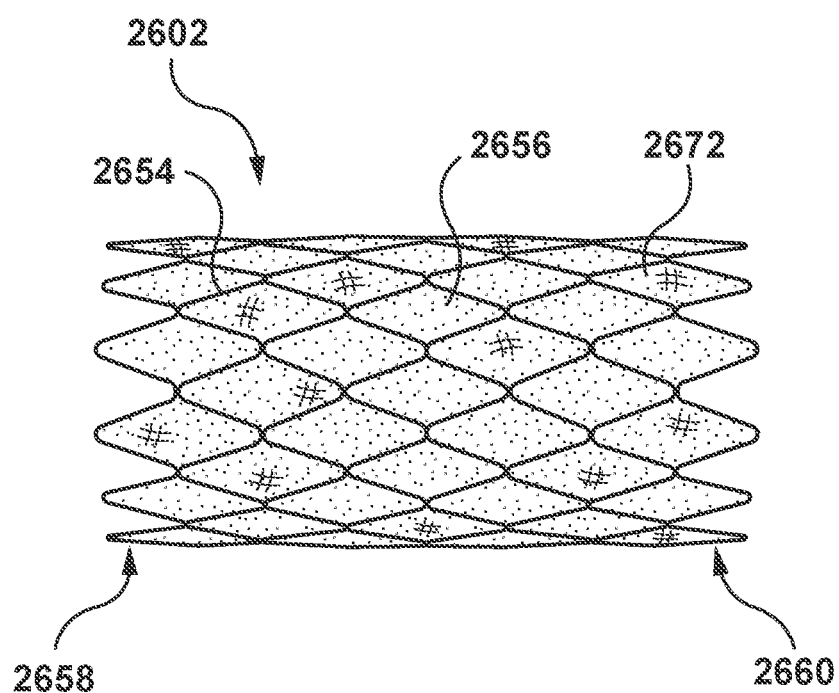
FIG. 26 is a side view of a docking frame to be used with the valve frame of FIG. 24, the docking frame being shown in its expanded configuration and being removed from the delivery system for illustrative purposes only.

Valve frame 2404 is shown in its expanded or deployed configuration in FIG. 24, and docking frame 2602 is shown in its expanded or deployed configuration in FIG. 26, removed from the delivery system for illustrative purposes only. Similar to first and second frames 102, 104 described above, docking and valve frames 2602, 2404 each include a self-expanding scaffold 2654, 2464, respectively, that returns to an expanded deployed state from a compressed or constricted delivery state. In this embodiment, self-expanding scaffolds 2654, 2464 are tubular components having proximal ends or segments 2658, 2468, respectively, and distal ends or segments 2660, 2470, respectively, with diamond-shaped openings 2656, 2466, respectively, that may be formed by a laser-cut manufacturing method and/or another conventional stent/scaffold forming method as would be understood by one of ordinary skill in the art. In this embodiment, docking and valve frames 2602, 2404 each include a tubular body or graft material 2672, 2472, respectively, attached to an inner or outer surface of scaffold 2654, 2464, respectively. Graft material 2672, 2472 may be formed from any suitable biocompatible material, for example and not limited to, a low-porosity woven or knit polyester, DACRON®, polytetrafluoroethylene (PTFE), polyurethane, silicone, or other suitable materials described above with respect to graft material 1672.

In this embodiment, valve frame 2404 includes a prosthetic valve component 2473 disposed within and secured to scaffold 2464. Prosthetic valve component 2473 is the same as prosthetic valve component 1673 described above, and includes at least two valve leaflets 2474 disposed within and secured to scaffold 2464. Valve frame 2404 and prosthetic valve component 2473 may be collectively referred to herein as a valve prosthesis 2475. Docking frame 2602 is sized or configured to receive valve prosthesis 2475. More particularly, docking frame 2602 is configured to fit and conform to the anatomy when expanded or deployed in situ in order to prevent paravalvular leakage (PVL) and valve prosthesis 2475 is implanted into docking frame 2602. As such, docking frame 2602 may be designed, sized, or otherwise configured to fit and conform to native heart anatomy at any desired valve location (i.e., aortic, mitral, tricuspid, pulmonic).

Figure 27:
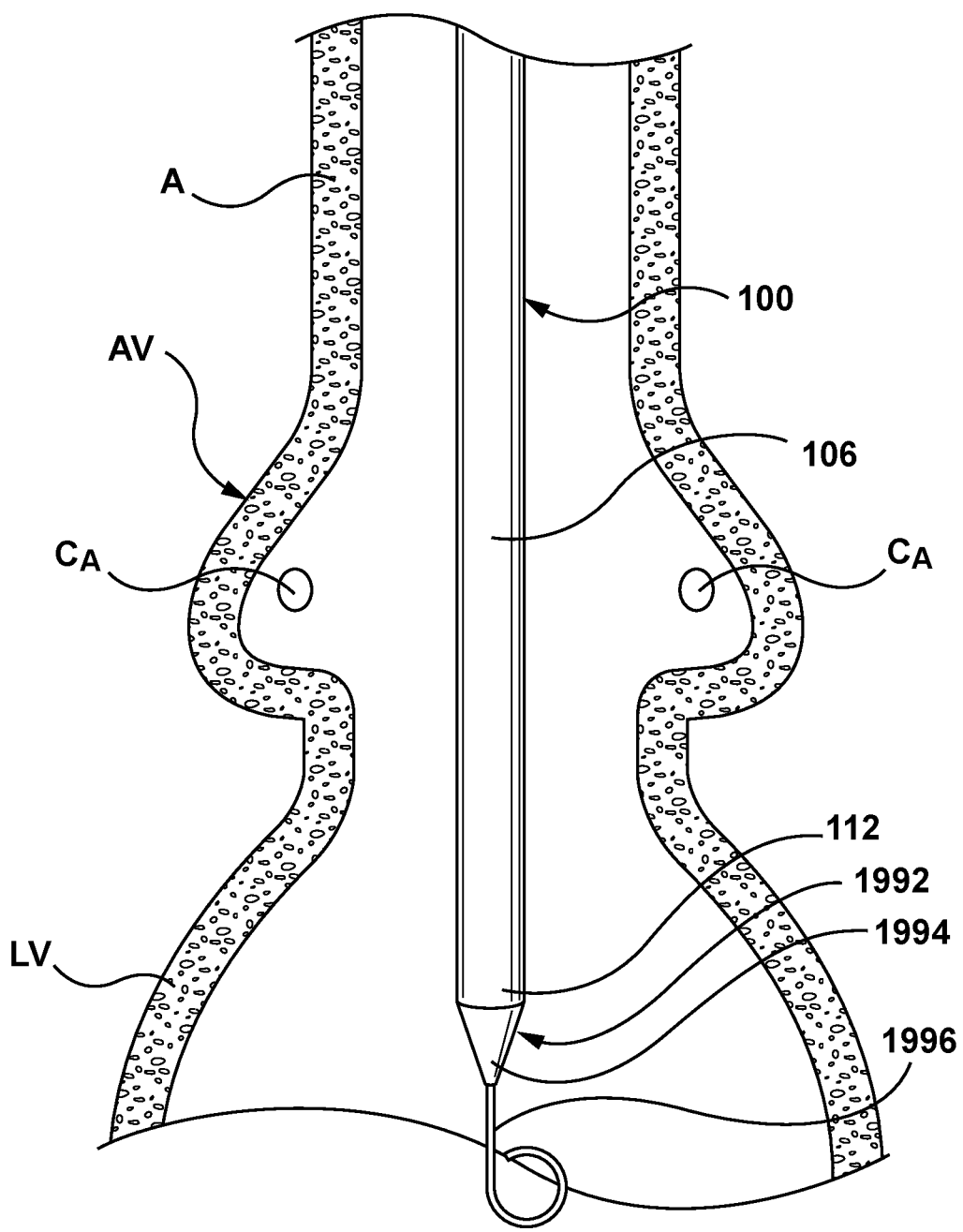
FIG. 27 illustrates a step for implanting the valve prosthesis of FIG. 24, wherein the step includes delivery of the delivery system with the outer sheath thereof in a non-retracted, delivery configuration such that the docking and valve frames are held in a compressed delivery configuration therein.

FIGS. 27-33 illustrate an exemplary method of implanting the above-described docking frame 2602 and valve frame 2404 within a native valve according to an embodiment hereof. As described above with respect to FIG. 5, when in the compressed delivery configuration, docking and valve frames 2602, 2404 are mounted in series with the proximal end of distal or docking frame 2602 overlapping the distal end of proximal or valve frame 2404 at an overlap region. Docking and valve frames 2602, 2404 are held in a radially compressed configuration via outer sheath component 106. The radially compressed configurations of docking and valve frames 2602, 2404 are suitable for percutaneous delivery within a vasculature. As shown in FIG. 27, in accordance with techniques known in the field of interventional cardiology and/or interventional radiology, delivery system 100 having a plunger 1992 disposed there-through is transluminally advanced in a retrograde approach over a guidewire 1996 through the vasculature to the treatment site, which in this instance is a target diseased native aortic valve AV that extends between a patient's left ventricle LV and a patient's aorta A. The coronary arteries $C_A$ are also shown on the sectional view of FIG. 27. Plunger 1992 includes a dilator tip 1994 at a distal end thereof. Delivery of delivery system 100 to the native aortic valve AV may be accomplished via a percutaneous transfemoral approach or may be positioned within the desired area of the heart via different delivery methods known in the art for accessing heart valves. During delivery, i.e., while being tracked over guidewire 1996, docking and valve frames 2602, 2404 remain compressed within an outer sheath component 106 of delivery system 100. Delivery system 100 is advanced until distal end 112 of outer sheath component 106 is distal to the native aortic valve AV and disposed within the left ventricle LV as shown in FIG. 27. In an embodiment, delivery system 100 is advanced approximately 5 mm into the left ventricle LV.

Figure 28:
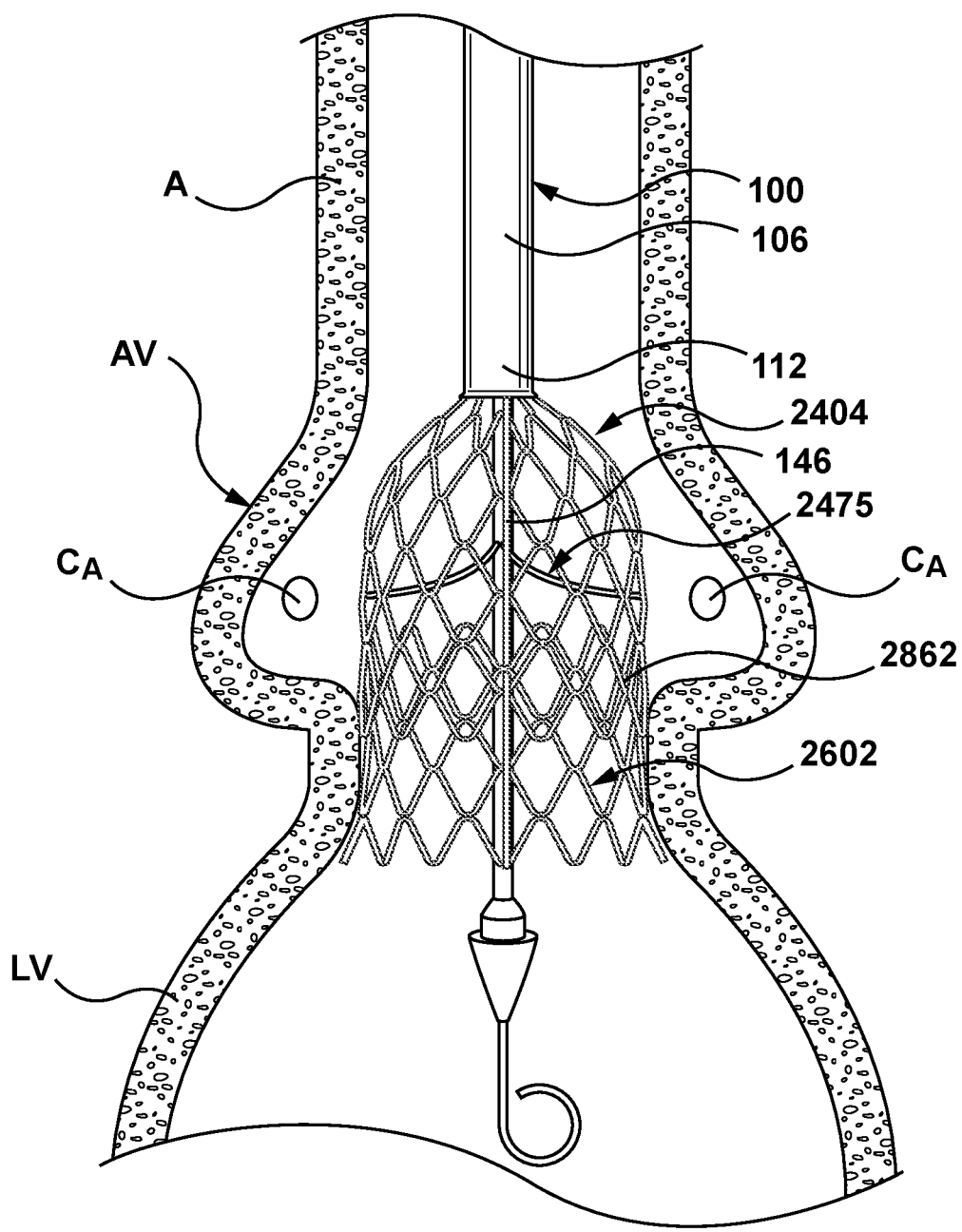
FIG. 28 illustrates a step for implanting the valve prosthesis of FIG. 16, wherein the step includes proximal retraction of the outer sheath to expand or deploy the docking and valve frames.

Once delivery system 100 is positioned as desired, outer sheath component 106 is proximally retracted in order to radially expand or deploy docking and valve frames 2602, 2404 as shown in FIG. 28. At this stage of deployment, flat wires 146 are woven through overlapping openings 2656, 2466 of docking and valve frames 2602, 2404 along a circumferential overlap region 2862 in order to releasably couple docking and valve frames 2602, 2404 together as described with respect to FIG. 6. The graft material of docking and valve frames 2602, 2404 is not shown in FIGS. 28-33 for sake of clarity. When outer sheath component 106 is proximally retracted to uncover docking and valve frames 2602, 2404, flat wires 146 slow the self-expansion of docking and valve frames 2602, 2404 to control deployment thereof. When docking frame 2602 is at least partially expanded distal of outer sheath component 106 while remaining coupled to valve frame 2404 by flat wires 146, docking frame 2602 is recapturable by outer sheath component 106 being distally advanced over flat wires 146. More particularly, if repositioning of docking frame 2602 is desired, outer sheath component 106 may be distally advanced over flat wires 146 in order to recapture docking and valve frames 2602, 2404 within outer sheath component 106. When recaptured, docking and valve frames 2602, 2404 resume their compressed, delivery configuration described above with respect to FIG. 5 and docking frame 2602 may be repositioned.

Figure 29:
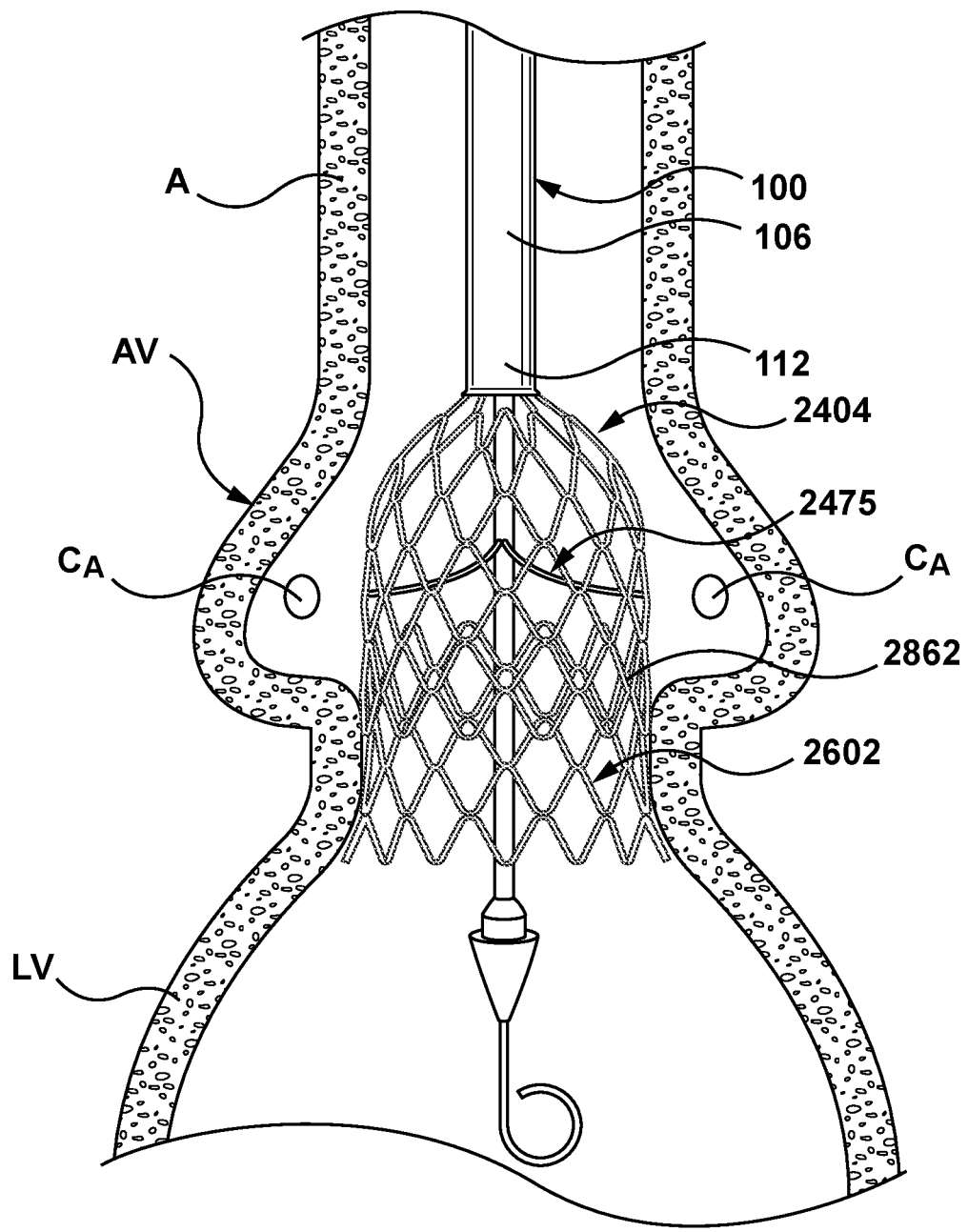
FIG. 29 illustrates a step for implanting the valve prosthesis of FIG. 16, wherein the step includes proximal retraction of the flat wires to decouple the docking and valve frames.

Once docking frame 2602 is positioned as desired (i.e., repositioning is no longer desired and recapturability is thus no longer required), flat wires 146 are proximally retracted in order to decouple docking frame 2602 from valve prosthesis 2475 and delivery system 100 as shown in FIG. 29. More particularly, elongate tube 136 having flat wires 146 attached thereto is proximally retracted relative to inner shaft 116 until distal ends 150 of flat wires 146 are positioned proximal to valve prosthesis 2475. Proximal retraction of flat wires 146 from docking frame 2602 releases docking frame 2602 from delivery system 100.

Figure 30:
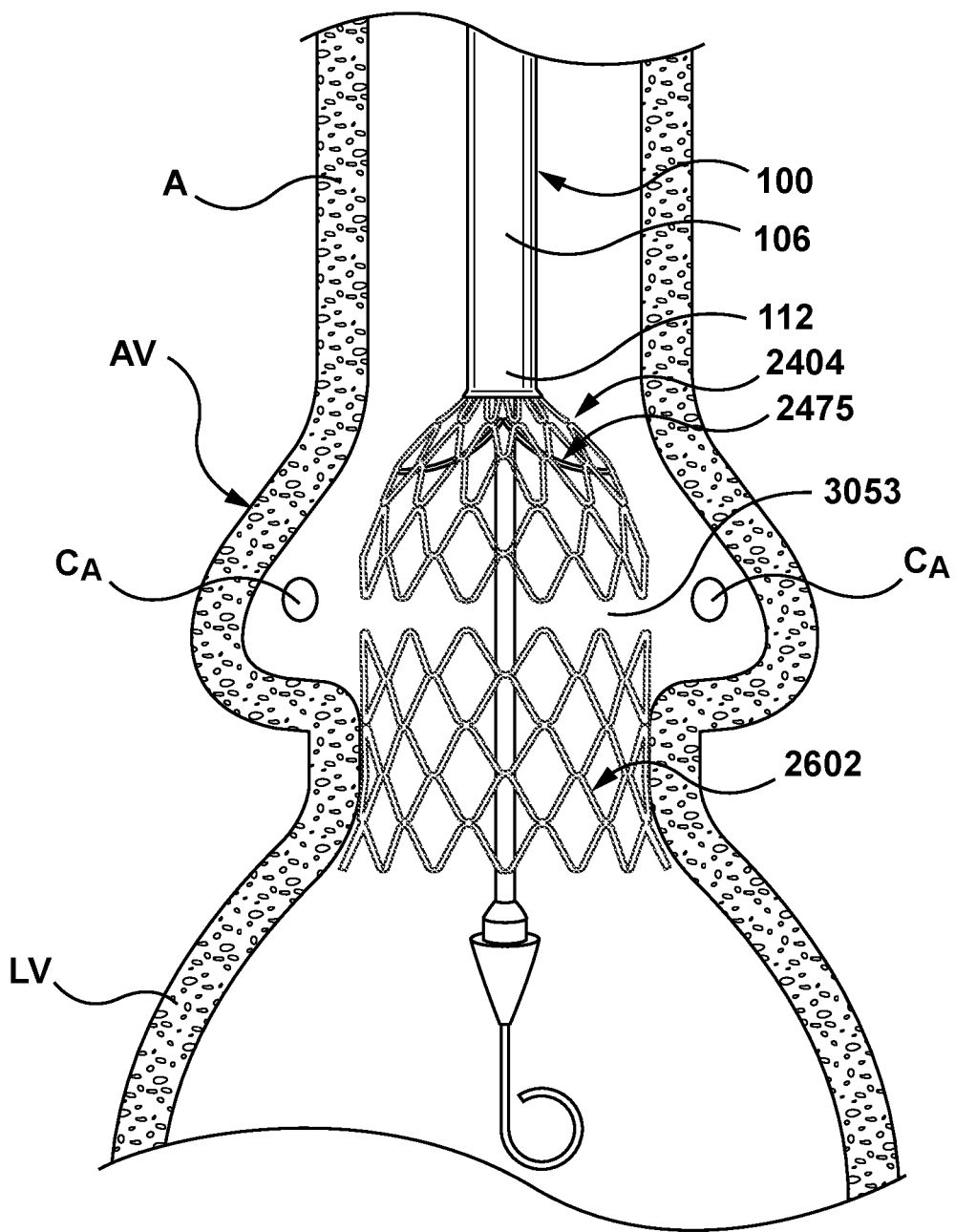
FIG. 30 illustrates a step for implanting the valve prosthesis of FIG. 16, wherein the step includes proximal retraction of the valve frame to separate the valve frame from the docking frame.

After docking frame 2602 is decoupled from delivery system 100, valve frame 2404 is proximally retracted in order to separate docking and valve frames 2602, 2404. More particularly, as described above with respect to FIG. 25, valve frame 2404 is releasably coupled to inner shaft 116 to be slideable therewith at this stage of deployment. Paddles 2586 (shown on FIG. 25) of valve frame 2404 are configured to mate or be received within recesses 2584 of distal hub 2582 to couple valve frame 2404 to inner shaft 116. In order to proximally retract valve frame 2404, inner shaft 116 having valve frame 2404 coupled thereto is proximally retracted relative to elongate tube 136 until a gap or space 3053 spans between docking and valve frames 2602, 2404 as shown in FIG. 30. As described above, prior to separation thereof, the distal end of valve frame 2404 is disposed within the proximal end of docking frame 2602. As such, at this stage of deployment, docking frame 2602 is expanded into apposition with the native valve and thus remains in position when valve frame 2404 is proximally retracted and detached therefrom.

Figure 31:
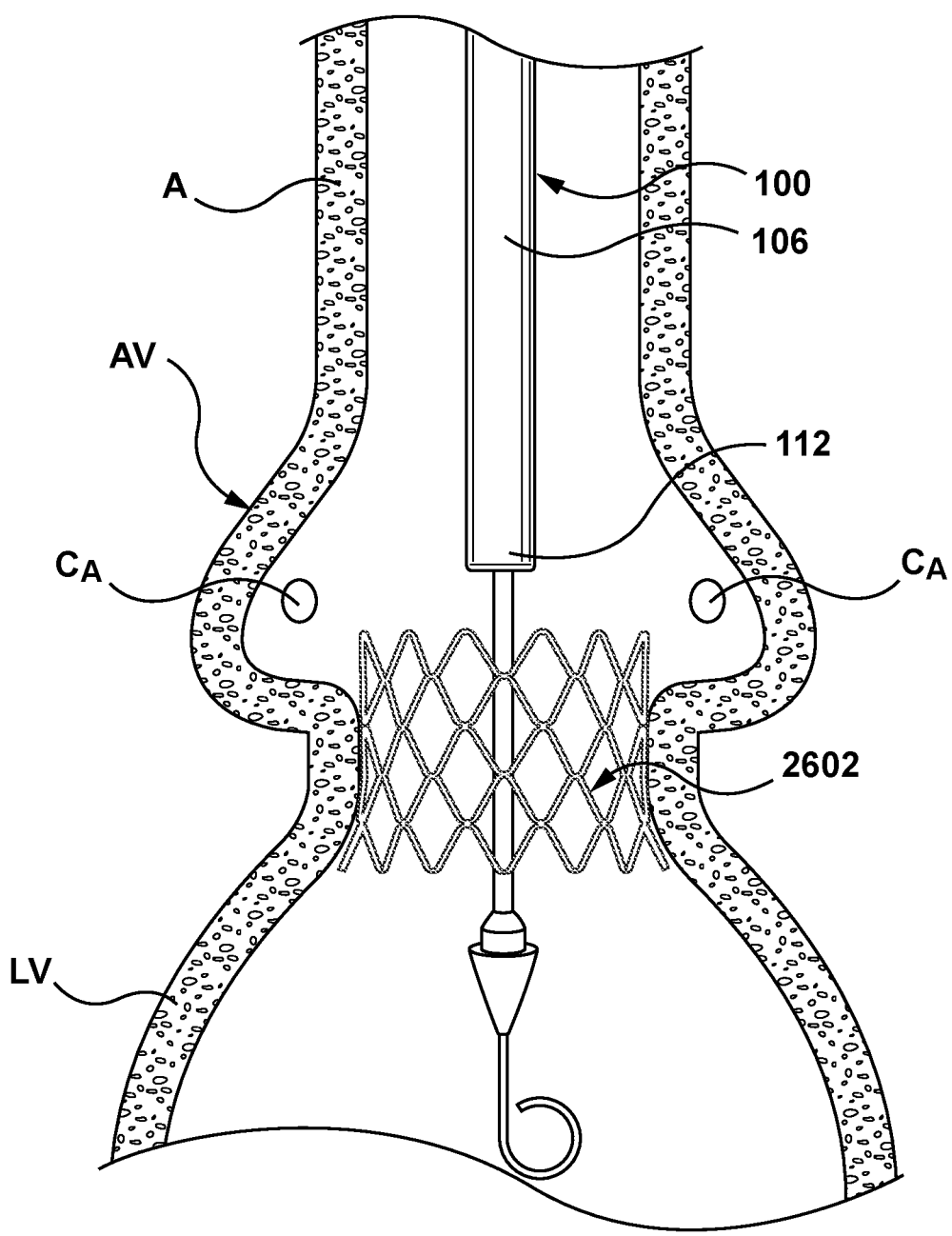
FIG. 31 illustrates a step for implanting the valve prosthesis of FIG. 16, wherein the step includes proximal retraction of the valve frame into the outer sheath to recapture the valve frame.
Figure 32:
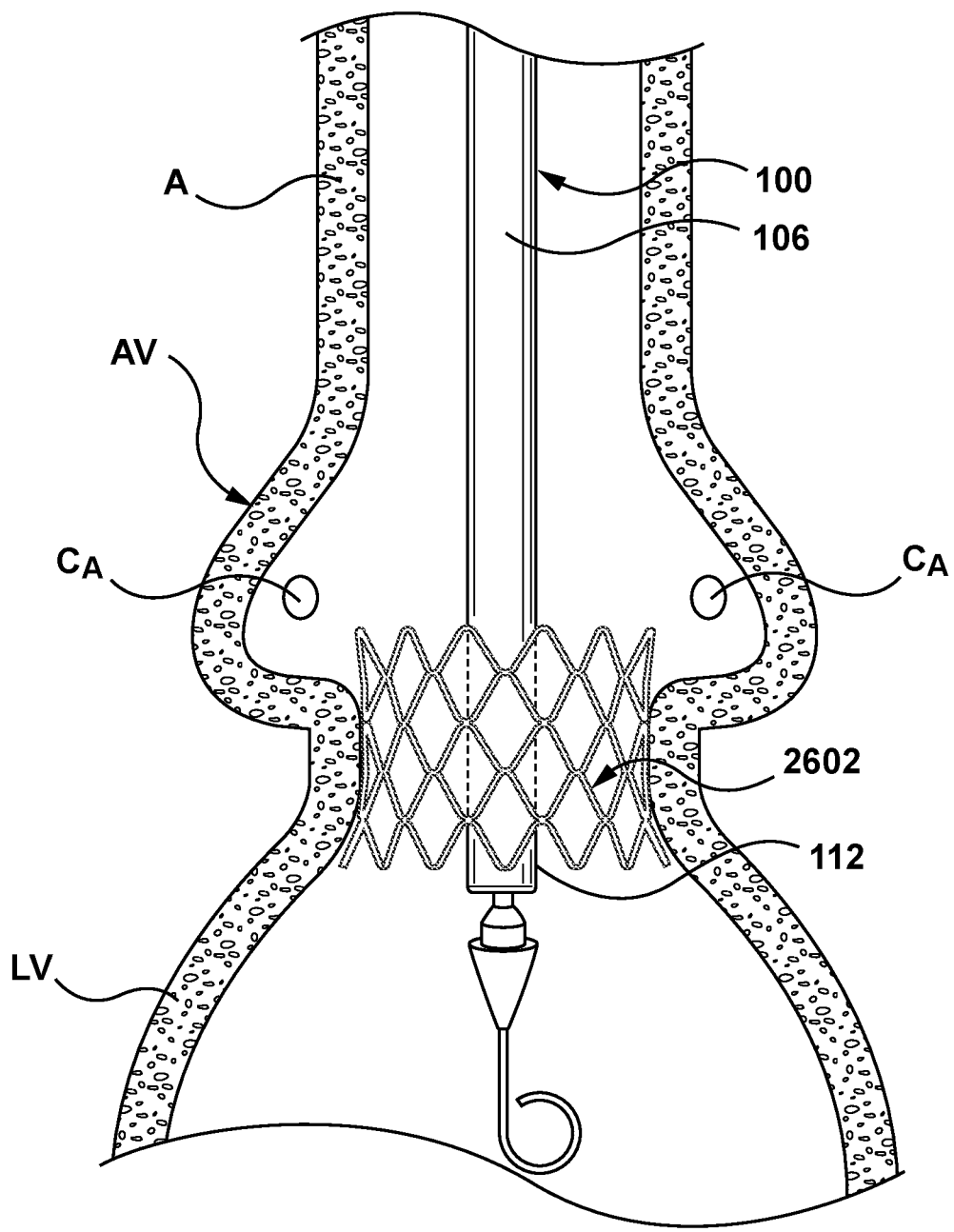
FIG. 32 illustrates a step for implanting the valve prosthesis of FIG. 16, wherein the step includes distal advancement of the outer sheath and valve frame compressed therein to position the valve frame within the deployed docking frame.
Figure 33:
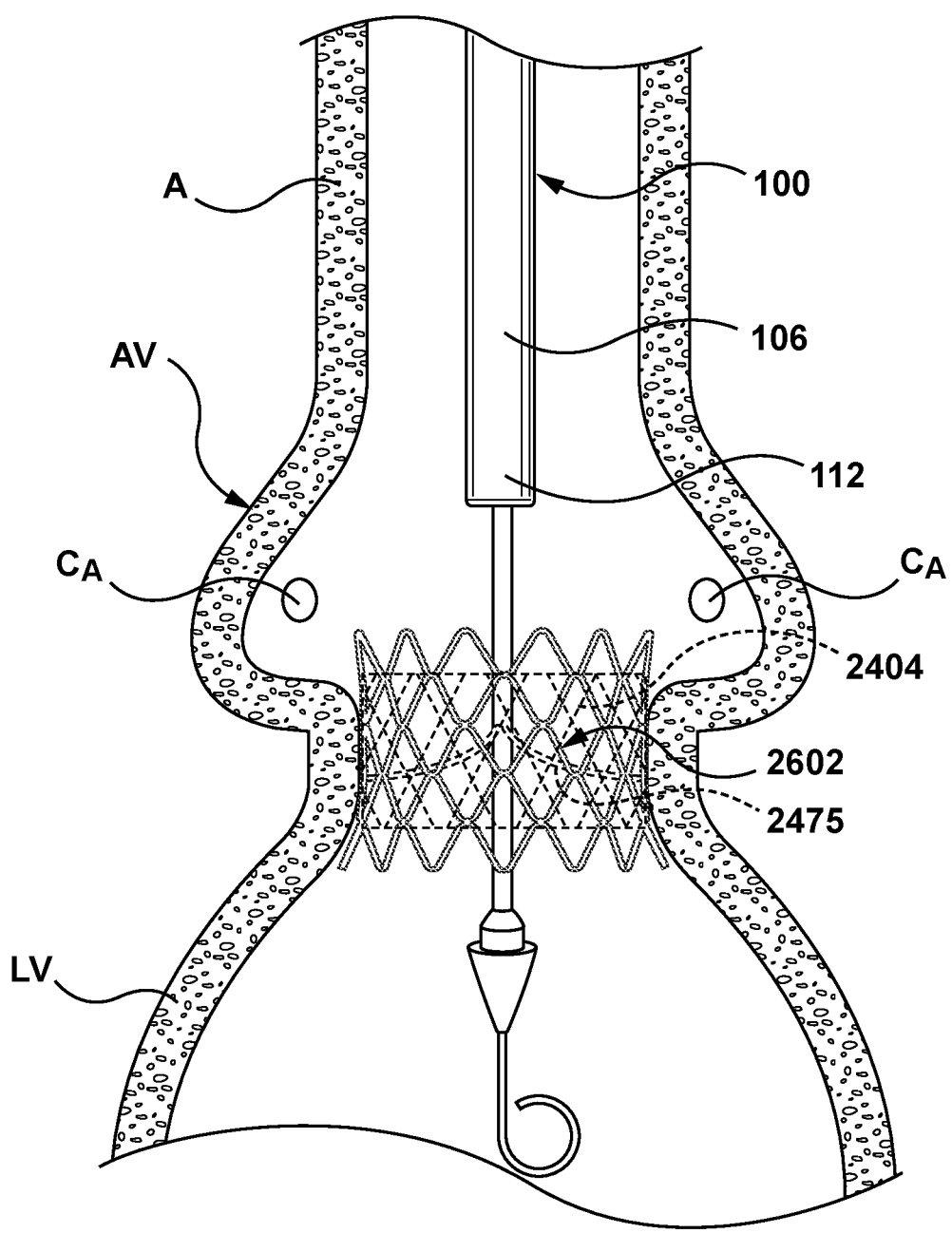
FIG. 33 illustrates a step for implanting the valve prosthesis of FIG. 16, wherein the step includes proximal retraction of the outer sheath to expand and deploy the valve frame within the deployed docking frame.

After docking and valve frames 2602, 2404 are separated from each other, inner shaft 116 is further proximally retracted relative to outer sheath component 106 in order to recapture valve frame 2404 as shown in FIG. 31. Valve prosthesis 2475 is still releasably coupled to inner shaft 116 at this stage of deployment such that valve prosthesis 2475 is slideable with inner shaft 116. As inner shaft 116 is pulled into outer sheath component 106, if not previously retracted into outer sheath component 106, flat wires 146 are also further proximally retracted relative to outer sheath component 106 in order to be recaptured with valve frame 2404. In FIG. 31, valve prosthesis 2475 is shown fully recaptured with outer sheath component 106. Once valve prosthesis 2475 is fully recaptured within outer sheath component 106, valve prosthesis 2475 is ready to be positioned for deployment thereof. Thus, in FIG. 32, delivery system 100 (with outer sheath component 106 having valve prosthesis 2475 radially compressed therein) is distally advanced to position valve prosthesis 2475 within deployed docking frame 2602. When valve prosthesis 2475 is positioned as desired, i.e., is longitudinally aligned and concentrically aligned within docking frame 2602, outer sheath component 106 is proximally retracted in order to radially expand or deploy valve frame 2404 into apposition with docking frame 2602 as shown in FIG. 33. As described above with respect to FIG. 25, when valve prosthesis 2475 is released from outer sheath component 106 for deployment, self-expansion of valve frame 2404 causes paddles 2586 to release or exit out of recesses 2584 to decouple valve prosthesis 2475 from inner shaft 116.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for transcatheter implantation of a heart valve prosthesis comprising:
    an outer sheath component defining a lumen therethrough;
    an elongate tube defining a lumen and having at least two wires longitudinally extending from a distal end thereof, the elongate tube and the at least two wires being slidably disposed within the lumen of the outer sheath component;
    an inner shaft slidably disposed within the lumen of the elongate tube;
    a valve prosthesis having a valve frame that is self-expanding with a prosthetic valve component secured therein; and
    a docking frame that is self-expanding, wherein the docking frame is disposed distal of the valve prosthesis when each is held in a compressed delivery configuration within a distal portion of the outer sheath component,
    wherein in the compressed delivery configuration the valve frame is releasably coupled to a distal end of the inner shaft to be slidable therewith relative to the elongate tube and the at least two wires longitudinally extend along exterior portions of the valve frame and the docking frame and are woven through adjacent distal and proximal ends of the valve frame and the docking frame, respectively, to releasably couple them to each other.

2. The system of claim 1, wherein the docking frame is configured to be released from and implanted by the delivery system at an implantation site and thereafter the valve prosthesis is configured to be released from and implanted by the delivery system within the docking frame.

3. The system of claim 1, wherein when the outer sheath component is proximally retracted to uncover the docking frame the at least two wires slow the self-expansion of the docking frame to control deployment thereof.

4. The system of claim 3, wherein when the outer sheath component is further proximally retracted to uncover the valve frame the at least two wires slow the self-expansion of the valve prosthesis.

5. The system of claim 1, wherein a proximal end of the valve frame is releasably coupled to a distal hub disposed at the distal end of the inner shaft.

6. The system of claim 1, wherein a distal segment of the valve frame is radially disposed within a proximal segment of the docking frame to provide a circumferential overlap region therebetween.

7. The system of claim 6, wherein the at least two wires are woven through overlapping openings of the docking and valve frames along the circumferential overlap region of the docking and valve frames to releasably couple them to each other.

8. The system of claim 7, wherein each of the at least two wires is woven through a first set of overlapping openings of the docking and valve frames within the circumferential overlap region of the docking and valve frames and through a second set of overlapping openings of the docking and valve frames within the circumferential overlap region of the docking and valve frames.

9. A system for transcatheter implantation of a heart valve prosthesis comprising:
    an outer sheath component defining a lumen therethrough;
    an elongate tube having at least two wires longitudinally extending from a distal end thereof, the elongate tube and the at least two wires being slidably disposed within the lumen of the outer sheath component;
    an inner shaft slidably disposed within the lumen of the elongate tube; and
    a first frame that is self-expanding and a second frame that is self-expanding, the first frame and the second frame being disposed in series within a distal portion of the outer sheath component and held in a compressed delivery configuration therein, wherein the first frame is distal of the second frame,
    wherein in the compressed delivery configuration the second frame is releasably coupled to a distal end of the inner shaft to be slidable therewith relative to the elongate tube and the at least two wires longitudinally extend along exterior portions of each of the first frame and the second frame and are woven through adjacent ends of each of the first frame and the second frame to releasably couple them to each other.

10. The system of claim 9, wherein when the outer sheath component is proximally retracted to uncover the first frame the at least two wires slow the self-expansion of the first frame to control deployment thereof.

11. The system of claim 10, wherein when the outer sheath component is further proximally retracted to uncover the second frame the at least two wires slow the self-expansion of the second frame.

12. The system of claim 11, wherein when each of the first frame and the second frame is at least partially expanded distal of the outer sheath component while remaining coupled to each other by the at least two wires, the first frame and the second frame are recapturable by the outer sheath component being distally advanced over the at least two wires.

13. The system of claim 11, wherein the at least two wires are flat and proximal retraction of the at least two flat wires from the first frame and the second frame releases at least the first frame from the delivery system.

14. The system of claim 9, further comprising:
a prosthetic valve component disposed within and secured to the second frame, and wherein the first frame is a docking frame that is configured to receive the second frame with the prosthetic valve component.

15. The system of claim 14, wherein the docking frame is configured to be released from and implanted by the delivery system at an implantation site and thereafter the second frame with the prosthetic valve component is configured to be released from and implanted by the delivery system within the docking frame.

16. The system of claim 9, wherein a proximal end of the second frame is releasably coupled to a distal hub disposed at the distal end of the inner shaft.

17. The system of claim 9, wherein a distal segment of the second frame is radially disposed within a proximal segment of the first frame to provide a circumferential overlap region therebetween.

18. The system of claim 17, wherein the at least two wires are woven through overlapping openings of the first and second frames along the circumferential overlap region of the first and second frames to releasably couple them to each other.

19. The system of claim 18, wherein each of the at least two wires is woven through a first set of overlapping openings of the first and second frames within the circumferential overlap region of the first and second frames and through a second set of overlapping openings of the first and second frames within the circumferential overlap region of the first and second frames.

20. A system for transcatheter implantation of a heart valve prosthesis comprising:
an outer sheath component defining a lumen therethrough;
an elongate tube defining a lumen and having at least two wires longitudinally extending from a distal end thereof, the elongate tube and the at least two wires being slidably disposed within the lumen of the outer sheath component;
an inner shaft slidably disposed within the lumen of the elongate tube;
a valve prosthesis having a valve frame that is self-expanding with a prosthetic valve component secured therein, wherein a proximal end of the valve frame includes a plurality of paddles proximally extending therefrom; and
a docking frame that is self-expanding, wherein the docking frame is disposed distal of the valve prosthesis when each is held in a compressed delivery configuration within a distal portion of the outer sheath component,
wherein in the compressed delivery configuration a proximal end of the valve frame is releasably coupled to a distal hub disposed at a distal end of the inner shaft to be slidable therewith relative to the elongate tube, the distal hub including a plurality of recesses and the plurality of paddles of the valve frame are configured to be received within the plurality of recesses of the distal hub to releasably couple the valve frame to the inner shaft, and the at least two wires longitudinally extend along exterior portions of the valve frame and the docking frame and are woven through adjacent distal and proximal ends of the valve frame and the docking frame, respectively, to releasably couple them to each other.

* * * * *